US010638915B2

(12) United States Patent
Nishizawa

(10) Patent No.: US 10,638,915 B2
(45) Date of Patent: May 5, 2020

(54) SYSTEM FOR MOVING FIRST INSERTABLE INSTRUMENT AND SECOND INSERTABLE INSTRUMENT, CONTROLLER, AND COMPUTER-READABLE STORAGE DEVICE

(71) Applicant: OLYMPUS CORPORATION, Tokyo (JP)

(72) Inventor: Koji Nishizawa, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 106 days.

(21) Appl. No.: 15/976,142

(22) Filed: May 10, 2018

(65) Prior Publication Data

US 2018/0256008 A1    Sep. 13, 2018

Related U.S. Application Data

(63) Continuation of application No. PCT/JP2016/083788, filed on Nov. 15, 2016.

(30) Foreign Application Priority Data

Feb. 10, 2016  (JP) .................. 2016-023670

(51) Int. Cl.
*A61B 1/00* (2006.01)
*A61B 34/20* (2016.01)
(Continued)

(52) U.S. Cl.
CPC ...... *A61B 1/00006* (2013.01); *A61B 1/00149* (2013.01); *A61B 1/05* (2013.01);
(Continued)

(58) Field of Classification Search
CPC .................................................... A61B 1/00
See application file for complete search history.

(56) References Cited

U.S. PATENT DOCUMENTS 5,836,869 A   11/1998 Kudo et al.
6,036,637 A    3/2000 Kudo
(Continued)

FOREIGN PATENT DOCUMENTS

JP      8-336497 A   12/1996
JP   2000-32442 A    1/2000
(Continued)

OTHER PUBLICATIONS

Gluckman J, Nayar SK, Thoresz KJ. Real-time omnidirectional and panoramic stereo. InProc. of Image Understanding Workshop Nov. 1998 (vol. 1, pp. 299-303). (Year: 1998).*
(Continued)

*Primary Examiner* — Clifford Hilaire
(74) *Attorney, Agent, or Firm* — Scully, Scott, Murphy & Presser, P.C.

(57) ABSTRACT

A medical system having a first insertable instrument having a first image sensor; a second insertable instrument having a second image sensor; a first arm configured to move the first insertable instrument; and a controller configured to: acquire a position and orientation of the second insertable instrument in a predetermined coordinate system; calculate a position and direction of an optical axis of the second image sensor based on the position and orientation of the second insertable instrument; acquire a position and orientation of the first insertable instrument in the predetermined coordinate system; calculate a first operation amount of the first arm to move the first image sensor such that the optical axis of the second image sensor substantially coincides with an optical axis of the first image sensor, based on the position and orientation of the first insertable instrument; and control the first arm based on the first operation amount.

9 Claims, 16 Drawing Sheets

(51) Int. Cl.
*G06T 7/73* (2017.01)
*A61B 1/05* (2006.01)
*H04N 5/232* (2006.01)
*H04N 5/225* (2006.01)

(52) U.S. Cl.
CPC .............. *A61B 34/20* (2016.02); *G06T 7/73* (2017.01); *H04N 5/23203* (2013.01); *A61B 2034/2055* (2016.02); *A61B 2034/2072* (2016.02); *G06T 2207/10068* (2013.01); *G06T 2207/30204* (2013.01); *G06T 2207/30244* (2013.01); *H04N 2005/2255* (2013.01)

(56) References Cited

U.S. PATENT DOCUMENTS

| | | |
|---|---|---|
| 2012/0062717 A1 | 3/2012 | Kinouchi et al. |
| 2014/0163736 A1* | 6/2014 | Azizian ................. A61B 34/20 700/259 |
| 2014/0371527 A1 | 12/2014 | Sato |
| 2015/0145953 A1 | 5/2015 | Fujie et al. |
| 2016/0235493 A1* | 8/2016 | LeBoeuf, II ........... A61B 5/064 |
| 2018/0165833 A1* | 6/2018 | Inoue ....................... G06T 3/00 |

FOREIGN PATENT DOCUMENTS

| | | |
|---|---|---|
| JP | 2001-161638 A | 6/2001 |
| JP | 2003-127076 A | 5/2003 |
| JP | 3506809 B2 | 3/2004 |
| JP | 2004-136066 A | 5/2004 |
| JP | 2006-167867 A | 6/2006 |
| JP | 4179846 B2 | 11/2008 |
| JP | 2009-125392 A | 6/2009 |
| JP | 4656700 B2 | 3/2011 |
| JP | 2015-93 A | 1/2015 |
| JP | 2015-24025 A | 2/2015 |
| WO | 2011/142189 A1 | 11/2011 |
| WO | 2013/141155 A1 | 9/2013 |

OTHER PUBLICATIONS

International Search Report dated Jan. 24, 2017 received in PCT/JP2016/083788.

* cited by examiner

SYSTEM FOR MOVING FIRST INSERTABLE INSTRUMENT AND SECOND INSERTABLE INSTRUMENT, CONTROLLER, AND COMPUTER-READABLE STORAGE DEVICE

CROSS-REFERENCE TO RELATED APPLICATIONS

This application is a continuation of PCT International Application No. PCT/JP2016/083788, filed on Nov. 15, 2016, which claims priority to Japanese Patent Application No. 2016-023670, filed Feb. 10, 2016. The contents of the PCT International Application No. PCT/JP2016/083788 and Japanese Patent Application No. 2016-023670 are incorporated herein by reference.

BACKGROUND

Conventionally, surgery in which a treatment is performed while switching between a panoramic view observation of a situation of an observation target and a magnified observation of a part of the observation target is known.

For example, in Japanese Unexamined Patent Application, First Publication No. 2004-136066, an ultrasonic observation system including an ultrasonic probe for grasping a three-dimensional situation of an observation target and a holder thereof is disclosed.

In Japanese Unexamined Patent Application, First Publication No. 2001-161638, a surgical microscope capable of observing other image information during an observation using the surgical microscope is disclosed.

In Japanese Unexamined Patent Application, First Publication No. 2000-32442, an endoscope system including a treatment scope for acquiring a narrow-angle image of a treatment site and an observation endoscope for acquiring a wide-angle image of the treatment site is disclosed.

SUMMARY

According to a first aspect of the present invention, a medical system is provided. The medical system comprises: a first insertable instrument comprising a first image sensor; a second insertable instrument comprising a second image sensor; a first arm configured to support and move the first insertable instrument; and a controller configured to: acquire a position and orientation of the second insertable instrument in a predetermined coordinate system; calculate a position and direction of an optical axis of the second image sensor based on the position and orientation of the second insertable instrument; acquire a position and orientation of the first insertable instrument in the predetermined coordinate system; calculate a first operation amount of the first arm to move the first image sensor such that the optical axis of the second image sensor substantially coincides with an optical axis of the first image sensor, based on the position and orientation of the first insertable instrument; and control the first arm, based on the first operation amount of the first arm, to move the first insertable instrument.

According to a second aspect of the present invention, a controller for controlling a medical system comprising: a first insertable instrument comprising a first image sensor; a second insertable instrument comprising a second image sensor; and a first arm configured to support and move the first insertable instrument, is provided. The controller comprises one or more processors configured to: acquire a position and orientation of the second insertable instrument in a predetermined coordinate system; calculate a position and direction of an optical axis of the second image sensor based on the position and orientation of the second insertable instrument; acquire a position and orientation of the first insertable instrument in the predetermined coordinate system; calculate a first operation amount of the first arm to move the first image sensor such that the optical axis of the second image sensor substantially coincides with an optical axis of the first image sensor, based on the position and orientation of the first insertable instrument; and control the first arm, based on the first operation amount of the first arm, to move the first insertable instrument.

According to a third aspect of the present invention, a computer readable storage device storing instructions for controlling a medical system comprising: a first insertable instrument comprising a first image sensor; a second insertable instrument comprising a second image sensor; and a first arm configured to support and move the first insertable instrument, is provided. The instructions cause a computer to perform processes comprising: acquiring a position and orientation of the second insertable instrument in a predetermined coordinate system; calculating a position and direction of an optical axis of the second image sensor based on the position and orientation of the second insertable instrument; acquiring a position and orientation of the first insertable instrument in the predetermined coordinate system; calculating a first operation amount of the first arm to move the first image sensor such that the optical axis of the second image sensor substantially coincides with an optical axis of the first image sensor, based on the position and orientation of the first insertable instrument; and controlling the first arm, based on the first operation amount of the first arm, to move the first insertable instrument.

DETAILED DESCRIPTION

First Embodiment

Figure 1:
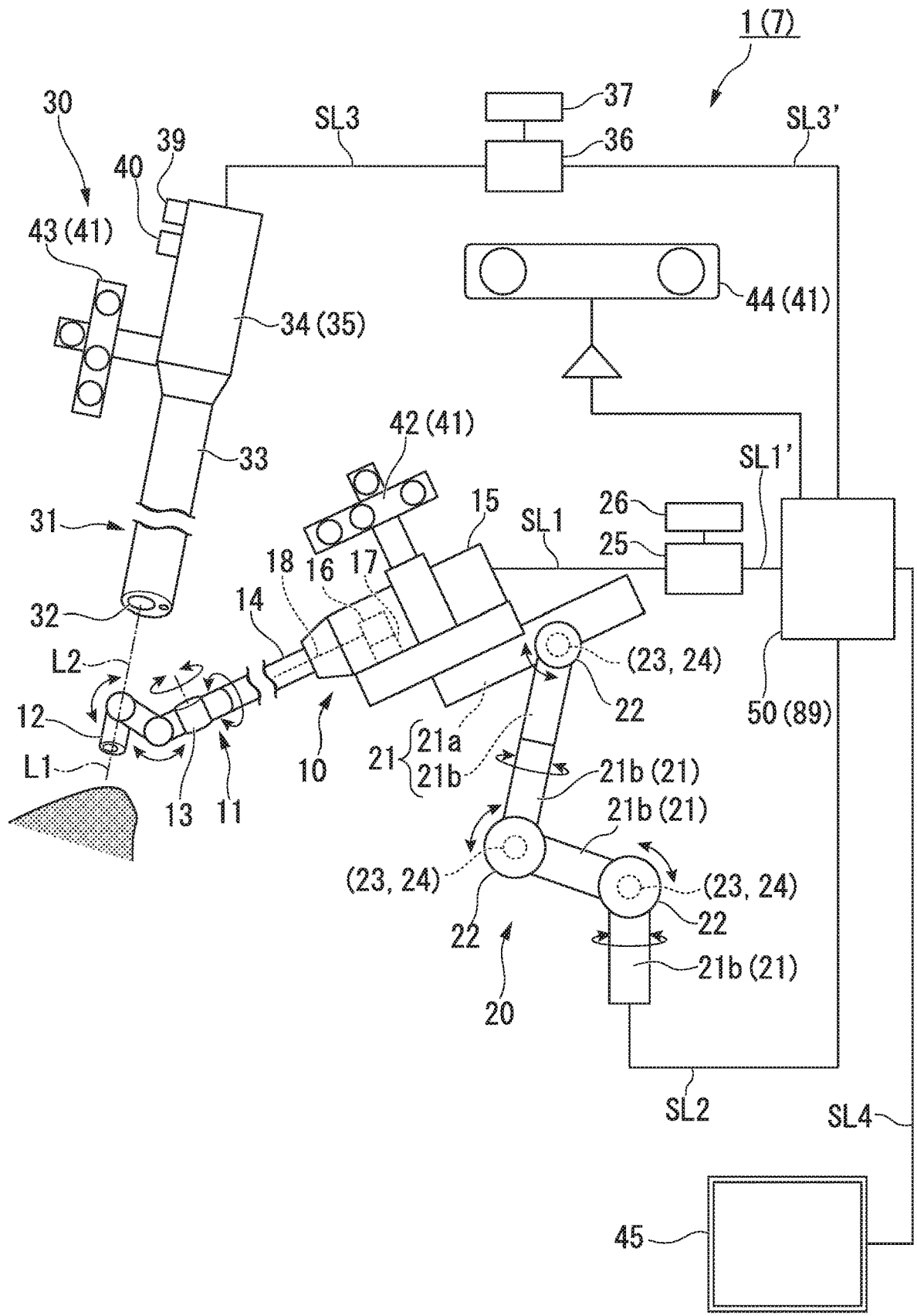
FIG. 1 is a schematic overall view of an endoscope system according to a first embodiment of the present invention.
Figure 2:
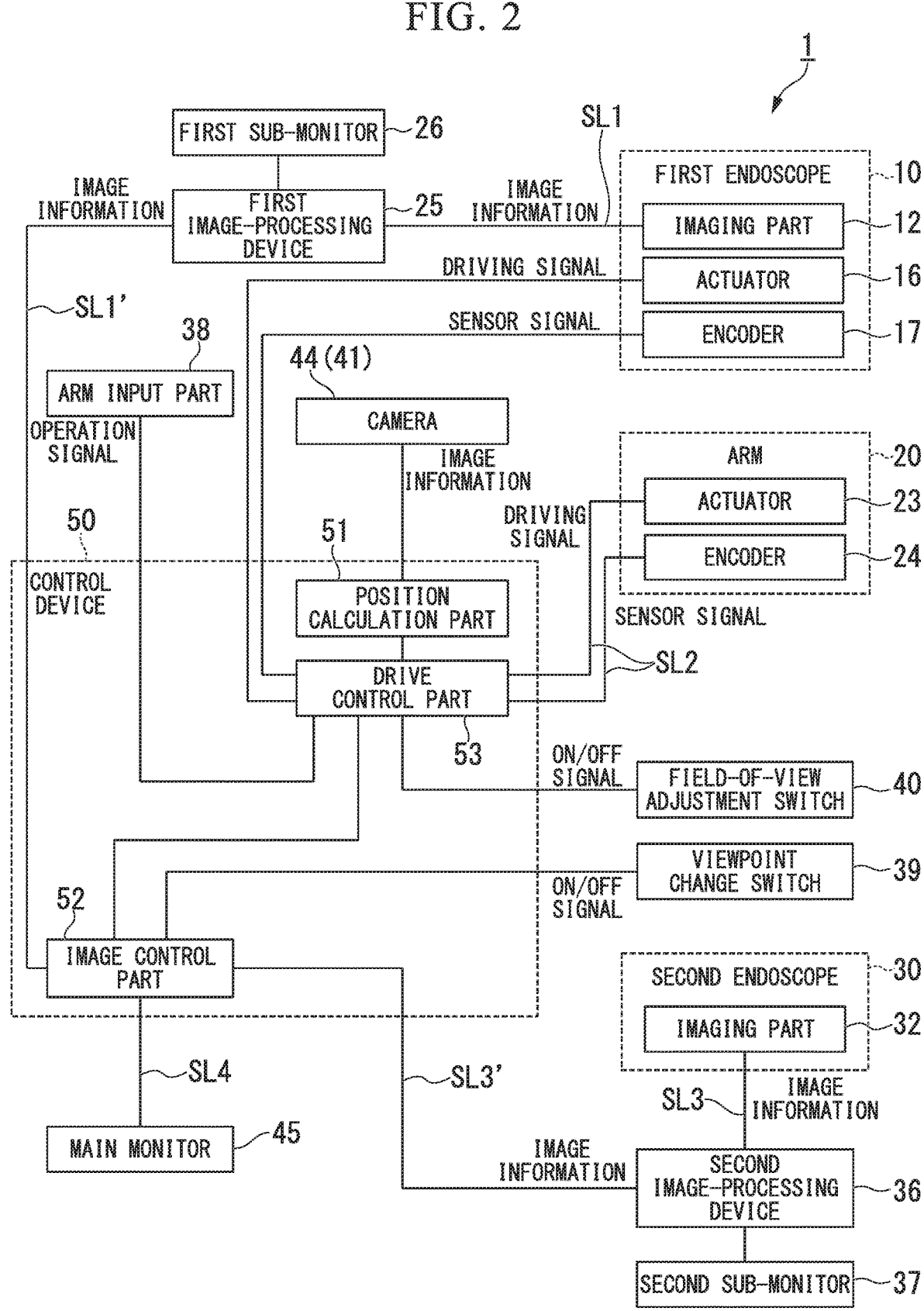
FIG. 2 is a block diagram of a main part of the endoscope system.
Figure 3:
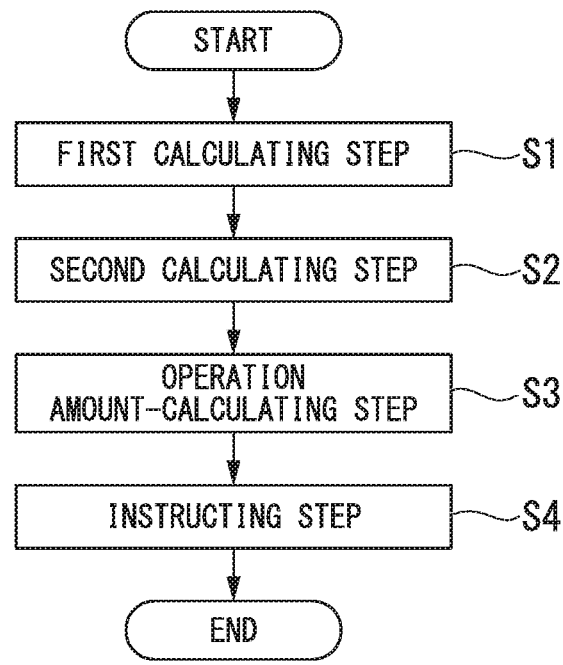
FIG. 3 is a flowchart illustrating a control procedure by a control device of the endoscope system.

A first embodiment of the present invention will be described. FIG. 1 is a schematic overall view of an endoscope system according to the present embodiment. FIG. 2 is a block diagram of a main part of the endoscope system. FIG. 3 is a flowchart illustrating a control procedure by a control device of the endoscope system. FIGS. 4 to 7 are views describing actions of the endoscope system.

An endoscope system 1 according to the present embodiment illustrated in FIG. 1 is a medical system used for surgery and the like.

As illustrated in FIG. 1, the endoscope system 1 includes a first endoscope 10, an arm 20, a first image-processing device 25, a first sub-monitor 26, a second endoscope 30, a second image-processing device 36, a second sub-monitor 37, a position-and-orientation-detecting device 41, a main monitor 45, and a control device 50 (also referenced throughout this disclosure as controller). The control device 50 can be realized by hardware such as one or more Central Processing Unit (CPU), and by reading instructions stored on a computer readable storage device.

In the endoscope system 1 according to the present embodiment, the first endoscope 10 is an endoscope for acquiring an image (narrow-angle image) with a narrow area including a treatment site as an imaging target and displaying the image on the first sub-monitor and the main monitor 45. The first endoscope 10 is connected to the first image-processing device 25 via a signal line SL1. Also, the first image-processing device 25 and the control device 50 are connected via a signal line SL1'.

The first endoscope 10 has an insertion part 11 and a driving part 15.

The insertion part 11 is an elongated part inserted into a patient's body, which is a treatment target, from outside the body.

The insertion part 11 has an imaging part 12 (first imaging part), a joint part 13, and a shaft part 14.

To acquire an image with a treatment site as an imaging target site, the imaging part 12 has, for example, an image sensor and an objective optical system (both of which are not illustrated). The image sensor of the imaging part 12 can, for example, acquire a bright field image of the imaging target site. The objective optical system of the imaging part 12 has a predetermined optical axis L1. A field-of-view center of the image captured by the imaging part 12 is a position of the optical axis L1 of the imaging part 12. The image captured by the imaging part 12 is transmitted to the first image-processing device 25 which will be described below and is also transmitted to the control device 50. A field angle of the imaging part 12 of the first endoscope 10 may be equal to a field angle of an imaging part 32 of the second endoscope 30 or may be different from the field angle of the imaging part 32 of the second endoscope 30. In the present embodiment, the narrow-angle image captured by the imaging part 12 of the first endoscope 10 is an image with a part of an image captured by the imaging part 32 of the second endoscope 30 as an imaging field of view, but the embodiments are not limited to meaning that the field angle of the imaging part 12 of the first endoscope 10 is narrower than the field angle of the imaging part 32 of the second endoscope 30.

The joint part 13 has a plurality of joint elements connected to each other via a rotation shaft. The joint part 13 is deformable to move the imaging part 12 with respect to the shaft part 14. Further, the joint part 13 is operable to adjust a position of the imaging part 12 and a direction of the imaging field-of-view thereof. An operation wire 18 configured to transmit power for operating the joint part 13 is connected to the joint part 13.

The shaft part 14 has a rigid cylindrical shape to guide the imaging part 12 to the vicinity of the treatment site in the body. A signal line (not illustrated) from the imaging part 12 and the operation wire 18 for connecting the joint part 13 to the driving part 15, which will be described below, to operate the joint part 13 are wired inside the shaft part 14.

The driving part 15 is arranged at an end portion of the insertion part 11 opposite to the imaging part 12 side (referred to as a proximal end portion of the first endoscope 10 in the present embodiment). The driving part 15 is fixed to the shaft part 14. The signal line (not illustrated) extending from the imaging part 12 and the operation wire 18 extending from the joint part 13 are wired inside the driving part 15. The driving part 15 has an actuator 16 connected to the operation wire 18 to move the operation wire 18, and an encoder 17 for detecting an operation amount of the actuator 16. The actuator 16 provided in the driving part 15 operates in accordance with control by the control device 50. The driving part 15 also has a function as an adapter for attaching the first endoscope 10 to the arm 20.

It is unnecessary for the first endoscope 10 of the present embodiment to have a structure for directly performing incision, suturing, or the like on the treatment site. The insertion part 11 may have a treatment tool (not illustrated) for performing incision, suturing, or the like on the treatment site at a distal end. The insertion part 11 may also have a channel for inserting a known treatment tool for an endoscope.

The first endoscope 10 may be able to rotate the imaging field of view of the imaging part 12 about the field-of-view center as the center of rotation (for example, about the optical axis L1 of the imaging part 12 as the center of rotation). The rotation of the imaging field-of-view may be configured to mechanically rotate the imaging part 12 or configured to rotate an image acquired by the image sensor of the imaging part 12 by image processing. By enabling such movement or rotation of the imaging field of view, an association between an image captured by the imaging part 32 of the second endoscope 30, which will be described below, and an image captured by the imaging part 12 of the first endoscope 10 may be facilitated.

The arm 20 holds the first endoscope 10 in a desired position and orientation or moves the first endoscope 10 in a desired direction. The arm 20 is connected to the control device 50 via a signal line SL2.

The arm 20 has link parts 21, joint parts 22, actuators 23, and encoders 24. The link parts 21 include a distal link part 21a having a detachable structure to which the driving part 15 of the first endoscope 10 is attachable, and a plurality of proximal link parts 21b configured to connect joint elements constituting the joint parts 22.

The joint parts 22 connect two adjacent link parts 21 such that the two adjacent link parts 21 are bendable, for example. Some of the joint parts 22 constituting the plurality of joint parts 22 may rotatably connect two adjacent link parts 21 such that center lines thereof are coaxial.

An upper limit of degrees of freedom of the arm 20 is not particularly limited. The arrangement, the number, or the like of the joint parts 22 may be such that a minimum necessary degree of freedom can be given to the arm 20 to control the position and orientation of the first endoscope 10.

As an example, the actuator 23 is arranged in the joint part 22. The actuator 23 operates the joint part 22 in accordance with operation control by the control device 50.

As an example, the encoders 24 are arranged in the plurality of joint parts 22. In the present embodiment, the encoders 24 are arranged in all of the joint parts 22 included in the arm 20.

The encoders 24 are electrically connected to the control device 50, which will be described below. The encoders 24 output movement amounts of the joint parts 22 to the control device 50. The encoders 24 may also output signals indicating absolute angles of the joint parts 22 to the control device 50.

As illustrated in FIG. 2, the first image-processing device 25 is connected to the imaging part 12 of the first endoscope 10. The first image-processing device 25 receives image information captured by the imaging part 12 of the first endoscope 10 from the imaging part 12, outputs the image information to the first sub-monitor 26 as a video signal, and outputs the image information to an image control part 52 of the control device 50.

The first sub-monitor 26 displays a video on the basis of the video signal output from the first image-processing device 25. The first sub-monitor 26 may display a narrow-angle image including a treatment site.

In the endoscope system 1 according to the present embodiment, the second endoscope 30 is an endoscope for acquiring an image (wide-angle image) with a wide area including a treatment site as an imaging target and displaying the image on the second sub-monitor and the main monitor 45. The second endoscope 30 is connected to the second image-processing device 36 via a signal line SL3. Also, the second image-processing device 36 and the control device 50 are connected via a signal line SL3'.

The second endoscope 30 has an insertion part 31 and an operation part 34.

The insertion part 31 of the second endoscope 30 has a thin, long rod shape as a whole. In the present embodiment, the insertion part 31 of the second endoscope 30, for example, has a property of being rigid. That is, in the present embodiment, the second endoscope 30 is a rigid mirror.

The insertion part 31 of the second endoscope 30 has the imaging part 32 (second imaging part) and a shaft part 33.

To acquire an image of a treatment site, the imaging part 32 of the second endoscope 30 has, for example, an image sensor and an objective optical system (both of which are not illustrated). The image sensor of the imaging part 32 of the second endoscope 30 can, for example, acquire a bright field image of an imaging target site. The objective optical system of the imaging part 32 has a predetermined optical axis L2. A field-of-view center of the image captured by the imaging part 32 is a position of the optical axis L2 of the imaging part 32. The image captured by the imaging part 32 of the second endoscope 30 is transmitted to the control device 50, which will be described below. A field angle of the imaging part 32 of the second endoscope 30 may be equal to a field angle of the imaging part 12 of the first endoscope 10 or may be different from the field angle of the imaging part 12 of the first endoscope 10. In the present embodiment, the wide-angle image captured by the imaging part 32 of the second endoscope 30 is an image that captures an area wider than the imaging field of view of the imaging part 12 of the first endoscope 10, but the embodiments are not limited to meaning that the field angle of the imaging part 32 of the second endoscope 30 is wider than the field angle of the imaging part 12 of the first endoscope 10.

The shaft part 33 of the second endoscope 30 has a rigid cylindrical shape to guide the imaging part 32 of the second endoscope 30 to the vicinity of the treatment site in the body. A signal line (not illustrated) for connecting the imaging part 32 of the second endoscope 30 to the control device 50, which will be described below, is wired inside the shaft part 33 of the second endoscope 30.

To operate the second endoscope 30 from outside the body, the operation part 34 is arranged at an end portion of the insertion part 31 of the second endoscope 30 opposite to the imaging part 32 side (referred to as a proximal end portion of the second endoscope 30 in the present embodiment).

The operation part 34 has a gripping part 35.

The gripping part 35 is a portion that can be gripped by an operator who operates the second endoscope 30.

In the present embodiment, an operator can move the entire insertion part 31 of the second endoscope 30 by gripping and moving the gripping part 35. That is, in the present embodiment, it is possible for the operator to move an imaging field of view of the imaging part 32 of the second endoscope 30 by gripping and moving the gripping part 35 when using the second endoscope 30.

A viewpoint change switch 39 and a field-of-view adjustment switch 40, which will be described below, may be arranged in the gripping part 35.

The constitution of the second endoscope 30 is not limited to the above constitution. The second endoscope 30 may be a rigid mirror or a flexible endoscope having the imaging part 32 for capturing the wide-angle image. A field-of-view direction of the imaging part 32 of the second endoscope 30 is not limited to the above constitution as long as the direction is fixed by the insertion part 31 of the second endoscope 30 or can be grasped by the control device 50.

As illustrated in FIG. 2, the second image-processing device 36 is connected to the imaging part 32 of the second endoscope 30. The second image-processing device 36 receives image information captured by the imaging part 32 of the second endoscope 30 from the imaging part 32, outputs the image information to the second sub-monitor 37 as a video signal, and outputs the image information to the image control part 52 of the control device 50.

The second sub-motor 37 displays a video on the basis of the video signal output from the second image-processing device 36. The second sub-monitor 37 may display a wide-angle image including a treatment site.

As illustrated in FIG. 2, an arm input part 38 is connected to a drive control part 53 of the control device 50. The arm input part 38 is, for example, operated by a scopist and outputs a predetermined operation signal for operating the arm 20 to the drive control part 53.

The viewpoint change switch 39 is electrically connected to the image control part 52 of the control device 50.

The viewpoint change switch 39 is a changeover switch for selecting one desired image from the narrow-angle image obtained by the first endoscope 10 and the wide-angle image obtained by the second endoscope 30. For example, the viewpoint change switch 39 may be a push-button switch and, every time the viewpoint change switch 39 is pressed, an image displayed on the main monitor 45 may be switched to a wide-angle-image or a narrow-angle image.

The viewpoint change switch 39 may be arranged at a position at which a person who performs a treatment on a treatment site (for example, a surgeon), a person who operates the first endoscope 10 or the second endoscope 30 (for example, a scopist), or the like can easily operate the viewpoint change switch 39.

For example, the viewpoint change switch 39 may be attached to a medical instrument operated by a surgeon performing a treatment on a treatment site.

The viewpoint change switch 39 may also be arranged in the vicinity of the gripping part 35 of the second endoscope 30 (see FIG. 1). Because the viewpoint change switch 39 of the present embodiment is arranged at a position at which the viewpoint change switch 39 can be easily operated by an operator operating the second endoscope 30, the viewpoint can be easily changed during a treatment using the second endoscope 30.

The field-of-view adjustment switch 40 is electrically connected to the drive control part 53 of the control device 50.

The field-of-view adjustment switch 40 is a switch for inputting, to the drive control part 53 of the control device 50, an input for operating the first endoscope 10 so that a field-of-view center of the narrow-angle image obtained by the first endoscope 10 and a field-of-view center of the wide-angle image obtained by the second endoscope 30 coincide with each other.

The field-of-view adjustment switch 40 may be arranged at a position at which a person performing a treatment on a treatment site (for example, a surgeon), a person operating the first endoscope 10 or the second endoscope 30 (for example, a scopist), or the like can easily operate the field-of-view adjustment switch 40. For example, the field-of-view adjustment switch 40 may be arranged in the vicinity of the gripping part 35 of the second endoscope 30. The field-of-view adjustment switch 40 is a push-button switch and, every time the field-of-view adjustment switch 40 is pressed, an operation in which the control device 50 moves the first endoscope 10 so that a field-of-view center of a narrow-angle image is made to coincide with a field-of-view center of a wide-angle image is started.

Because the field-of-view adjustment switch 40 of the present embodiment is arranged at a position at which the field-of-view adjustment switch 40 can be easily operated by an operator operating the second endoscope 30, a field-of-view center of a narrow-angle image and a field-of-view center of a wide-angle image may be easily made to coincide during a treatment using the second endoscope 30.

The position-and-orientation-detecting device 41, for example, detects positions and orientations of the first endoscope 10 and the second endoscope 30 in a space such as an operating room in which the endoscope system 1 according to the present embodiment is installed.

The position-and-orientation-detecting device 41 has a first marker 42, a second marker 43, and a camera 44. Also, the position-and-orientation-detecting device 41 is connected to the control device 50, which will be described below.

The first marker 42 is arranged in the driving part 15 of the first endoscope 10. The first marker 42 is a marker different from the second marker 43 to distinguish between the first endoscope 10 and the second endoscope 30.

A constitution of the first marker 42 is not particularly limited as long as the first marker 42 can be captured by the camera 44 and can be recognized by the control device 50. For example, the first marker 42 may have a shape unique to the first marker 42, have a pattern of a predetermined shape, or emit predetermined light to the camera 44.

The second marker 43 is arranged in the operation part 34 of the second endoscope 30. The second marker 43 is a marker different from the first marker 42 to distinguish between the first endoscope 10 and the second endoscope 30.

A constitution of the second marker 43 is not particularly limited as long as the second marker 43 can be captured by the camera 44 and can be recognized by the control device 50. For example, the second marker 43 may have a shape unique to the second marker 43, have a pattern of a predetermined shape, or emit predetermined light to the camera 44.

Even if the first marker 42 and the third marker 43 cannot be distinguished from each other, it is not important as long as an association is performed when the endoscope system 1 is used and a position and orientation of each of the markers are always tracked when the endoscope system 1 is used.

The camera 44 captures an image including the first marker 42 and the second marker 43 and transmits an image to the control device 50. The camera 44 acquires a plurality of images having different fields of view. For example, the camera 44 may include two imaging devices having different fields of view. The camera 44 is fixed in a part of a space such as an operating room in which the endoscope system 1 is arranged. For example, by the camera 44 being fixed to a part of an operating room and capturing an image including the first marker 42 and the second marker 43, positions and orientations of the first marker 42 and the second marker 43 in a predetermined coordinate system (reference coordinate system) based on a position of the camera 44 can be detected.

The main monitor 45 is connected to the control device 50 via a signal line SL4. The main monitor 45 may display an image captured by the imaging part 12 of the first endoscope 10 and an image captured by the imaging part 32 of the second endoscope 30 via the image control part 52. In the present embodiment, the main monitor 45 displays one image selected from the image captured by the first endoscope 10 and the image captured by the second endoscope 30 via a switching input with respect to the viewpoint change switch 39. The display state on the main monitor 45 is controlled by the image control part 52 of the control device 50. A specific constitution of the main monitor 45 is not particularly limited. For example, a known display system that displays an image on the basis of an analog or digital video signal may be appropriately selected as the main monitor 45.

The control device 50 controls the arm 20 and the second endoscope 30. Further, the control device 50 causes the main monitor 45 to display an image from the first endoscope 10, an image from the second endoscope 30, or the like.

The control device 50 illustrated in FIGS. 1 and 2 includes a position calculation part 51, the image control part 52, and the drive control part 53.

The position calculation part 51 receives an image signal from the camera 44 and calculates positions of the first marker 42 and the second marker 43. The position calculation part 51 stores the positions and orientations of the first marker 42 and the second marker 43 in a predetermined coordinate system (reference coordinate system) based on a position of the camera 44 as coordinate information.

The image control part 52 is connected to the first image-processing device 25, the second image-processing device 36, the drive control part 53, the viewpoint change switch 39, and the main monitor 45. The image control part 52 generates predetermined information for operating the drive control part 53 by using image information output from the first image-processing device 25 and image information output from the second image-processing device 36 and outputs the predetermined information to the drive control part 53.

The image control part 52 acquires an image captured by the first endoscope 10 and an image captured by the second endoscope 30 and outputs an image corresponding to a switching input with respect to the viewpoint change switch 39 to the main monitor 45. The main monitor 45 may consist of two screens, a main screen and a sub-screen, and the image control part 52 may cause an image designated by the switching input with respect to the viewpoint change switch 39 to be displayed on the main screen and cause an image not selected by the switching input to be displayed on the sub-screen.

The drive control part 53 is connected to the position calculation part 51. The drive control part 53 is also connected to the actuator 16 and the encoder 17 of the first endoscope 10 and the actuators 23 and the encoders 24 of the arm 20. Further, the drive control part 53 is connected to the arm input part 38.

The drive control part 53 controls operations of the joint part 13 and the arm 20 of the first endoscope 10 on the basis of an operation signal generated by an operation on the arm input part 38 by the operator.

Next, detection and recognition of the position and orientation of the first endoscope 10 and the position and orientation of the second endoscope 30 will be described.

The position calculation part 51 recognizes the first marker 42 from an image captured by the camera 44 of the position-and-orientation-detecting device 41. The image to be transmitted from the camera 44 to the position calculation part 51 is a set of a plurality of images having different fields of view, and the position calculation part 51 recognizes the position and orientation of the first marker 42 in the reference coordinate system from the plurality of images. The first marker 42 is arranged in the driving part 15 of the first endoscope 10, and the position of the first endoscope 10 with respect to the position of the first marker 42 is pre-stored in the control device 50. Because of this, the position calculation part 51 may recognize the position and orientation of the first endoscope 10 on the basis of the position and orientation of the first marker 42. As an example, the position calculation part 51 uses a predetermined reference point in the driving part 15 of the first endoscope 10 as the position of the first endoscope 10. That is, the position calculation part 51 recognizes coordinates of the reference point of the first endoscope 10 in the reference coordinate system as the position of the first endoscope 10. Further, the position calculation part 51 uses a direction of the first marker 42 in the reference coordinate system as the orientation of the first endoscope 10.

By referring to the encoder 17 provided in the joint part 13 of the first endoscope 10, the drive control part 53 recognizes the position and orientation of the imaging part 12 arranged at a distal end portion of the joint part 13 in addition to the position and orientation of the first endoscope 10. For example, the drive control part 53 recognizes coordinates of a part of the imaging part 12 in the reference coordinate system as the position of the imaging part 12. Further, the drive control part 53 recognizes a direction of an optical axis in the reference coordinate system as the orientation of the imaging part 12.

That is, in the present embodiment, a first position and orientation detector configured to detect the position and orientation of the first endoscope 10 in the reference coordinate system is constituted by the position-and-orientation-detecting device 41, the position calculation part 51, and the drive control part 53. Further, in the present embodiment, the control device 50 is capable of detect positions and orientations of the first endoscope 10 and an optical axis thereof.

The position calculation part 51 recognizes the second marker 43 from an image captured by the camera 44 of the position-and-orientation-detecting device 41. The position calculation part 51 recognizes the position and orientation of the second marker 43 similarly to the recognition of the position and orientation of the first marker 42. The drive control part 53 recognizes coordinates of a part of the imaging part 32 of the second endoscope 30 in the reference coordinate system as the position of the imaging part 32 of the second endoscope 30. Further, the drive control part 53 recognizes a direction of an optical axis in the reference coordinate system as the orientation of the imaging part 32 of the second endoscope 30.

That is, in the present embodiment, a second position and orientation detector configured to detect the position and orientation of the second endoscope 30 in the reference coordinate system is constituted by the position-and-orientation-detecting device 41, the position calculation part 51, and the drive control part 53. Further, in the present embodiment, the control device 50 can detect the position and orientation of the optical axis L2 of the second endoscope 30.

Next, control of the first endoscope 10 and the arm 20 will be described with reference to FIG. 2.

The drive control part 53 receives an input to the arm input part 38 arranged in the gripping part 35 of the second endoscope 30 and operates the first endoscope 10 and the arm 20 on the basis of the input.

Further, the drive control part 53 receives an input to the field-of-view adjustment switch 40 arranged in the gripping part 35 of the second endoscope 30 and operates the first endoscope 10 and the arm 20 on the basis of the input.

As illustrated in FIG. 3, the drive control part 53 that received the input to the field-of-view adjustment switch 40 operates the first endoscope 10 and the arm 20 as shown in each step from Step S1 to Step S4.

First, the drive control part 53 recognizes the position and orientation of the first endoscope 10 in the reference coordinate system and the position and orientation of the optical axis L1 of the first endoscope 10 in the reference coordinate system (a first calculating step, Step S1).

Further, the drive control part 53 recognizes the position and orientation of the optical axis L2 of the second endoscope 30 in the reference coordinate system (a second calculating step, Step S2). Step S2 may be performed before Step S1 or performed after Step S1.

After Step S1 and Step S2, the drive control part 53 calculates an operation amount for operating the first endoscope 10 and the arm 20 such that the first endoscope 10 and the arm 20 approach the position and orientation of the optical axis L2 of the second endoscope 30 recognized in Step S2 (an operation amount-calculating step, Step S3).

In Step S3, the drive control part 53 sets a position deviated by a predetermined distance toward a front side in an optical axis direction from coordinates indicating the position of the optical axis L2 of the second endoscope 30 as a movement target position of the optical axis L1 of the first endoscope 10. That is, in Step S3, the drive control part 53 sets the movement target position of the optical axis L1 of the first endoscope 10 in an area between a distal end of the imaging part 32 of the second endoscope 30 and an imaging target site. In Step S3, the movement target position set by the drive control part 53 has coordinates of one point on the optical axis L2 of the second endoscope 30 in the reference coordinate system.

Figure 6:
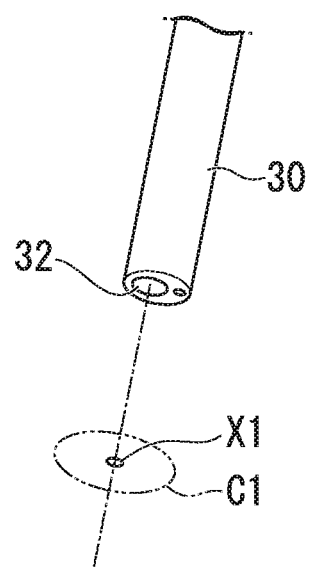
FIG. 6 is a view describing an action of the endoscope system.

The precision of the movement target position set by the drive control part 53 in Step S3 may not be that strict. This is because if the optical axis L1 of the first endoscope 10 and the optical axis L2 of the second endoscope 30 are parallel to each other, deviation between field-of-view centers on an image falls within an extent such that there is no practical problem even when the optical axes are spaced apart by some distance. For example, the movement target position set by the drive control part 53 in Step S3 may be set as an area of a certain range to allow a certain degree of error. For example, as illustrated in FIG. 6, a movement target position X1 set by the drive control part 53 in Step S3 may have coordinates along a plane orthogonal to the optical axis L2 of the second endoscope 30 in the reference coordinate system and within a circle C1 having a predetermined diameter about the optical axis. The movement target position set by the drive control part 53 in Step S3 may also have coordinates within a sphere whose center has coordinates of the position of the optical axis L2 of the second endoscope 30 in the reference coordinate system. The movement target position set by the drive control part 53 in Step S3 may also have coordinates within a cylinder whose center line is the optical axis L2 of the second endoscope 30 in the reference coordinate system.

In this case, because an error can be allowed when the position of the optical axis L1 of the first endoscope 10 is determined as having reached the optical axis L2 of the second endoscope 30, a case in which, for example, movement of the optical axis L1 of the first endoscope 10 cannot be completed due to movement of the optical axis L2 of the second endoscope 30 caused by hand shaking and the like of an operator operating the second endoscope 30 can be prevented. Further, in this case, when both the image from the first endoscope 10 and the image from the second endoscope 30 are caused to be displayed on the main monitor 45, image disturbance due to continuous movement of the imaging part 12 of the first endoscope 10 following the optical axis L2 of the second endoscope 30 caused by hand shaking when operating the second endoscope 30 can be reduced.

In Step S3, the drive control part 53 sets a movement path from a current position of the optical axis L1 of the first endoscope 10 to a movement target position. A method of setting the movement path from the current position of the optical axis L1 of the first endoscope 10 to the movement target position is not particularly limited as long as the method takes into consideration that there is no obstacle in the movement path. After the movement path of the optical axis L1 of the first endoscope 10 is set, the drive control part 53 calculates an operation amount of the arm 20 for moving the first endoscope 10 so that the optical axis moves along the movement path.

Further, in Step S3, the drive control part 53 sets an operation target direction of the imaging part 12 so that a direction of the optical axis L1 of the first endoscope 10 is made to coincide with a direction of the optical axis L2 of the second endoscope 30. In the present embodiment, in Step S3, the drive control part 53 calculates a joint driving amount of the joint part 13 for rotating the imaging part 12 around coordinates indicating the position of the optical axis L1 of the first endoscope 10 so that a direction of the optical axis L1 of the first endoscope 10 when the optical axis L1 of the first endoscope 10 is located at the movement target position is parallel to a direction of the optical axis L2 of the second endoscope 30. Further, the operation target direction of the imaging part 12 set by the drive control part 53 in Step S3 may be set as an area of a certain range to allow a certain degree of error.

In this way, in Step S3, the drive control part 53 calculates the operation amount of the arm 20 and the operation amount of the joint part 13.

This completes Step S3, and the procedure proceeds to Step S4.

Step S4 is an instructing step of outputting operation instructions for operating the arm 20 and the joint part 13 on the basis of the operation amount of the arm 20 and the operation amount of the joint part 13 calculated in Step 3 above to the arm 20 and the joint part 13.

In Step S4, the drive control part 53 operates the arm 20 and the joint part 13 by outputting operation instructions to the arm 20 and the joint part 13. For example, in Step S4, the drive control part 53 first outputs an operation instruction to the arm 20, thereby moving the first endoscope 10 until the position of the optical axis L1 of the first endoscope 10 reaches the movement target position on the optical axis L2 of the second endoscope 30. Then, the drive control part 53 outputs an operation instruction to the joint part 13, thereby rotating the imaging part 12 of the first endoscope 10 on the optical axis L2 of the second endoscope 30 until the optical axis L1 of the first endoscope 10 is coaxial with the optical axis L2 of the second endoscope 30.

Here, to move the arm 20 and the joint part 13 in the operation direction calculated in Step S3, the drive control part 53 calculates operation amounts of each degree of freedom of the joint part 13 and the arm 20 by using inverse kinematics and determines a control amount of each of the actuators. The drive control part 53 outputs a driving signal on the basis of the control amount.

After the output of the operation instructions is completed, the drive control part 53 determines, by the encoders 24 and 17 that detect orientations of the arm 20 and the joint part 13, whether the optical axis L1 of the first endoscope 10 has reached the movement target position, and when the drive control part 53 determines that the optical axis L1 of the first endoscope 10 reached the movement target position, Step S4 is completed.

In this way, by the operation procedure from Step S1 to Step S4 above, the drive control part 53 operates the first endoscope 10 and the arm 20 so that the optical axis L1 of the first endoscope 10 and the optical axis L2 of the second endoscope 30 become coaxial with each other corresponding to the input to the field-of-view adjustment switch 40.

An action of the endoscope system 1 according to the present invention will be described together with an operation when the endoscope system 1 is used.

Figure 4:
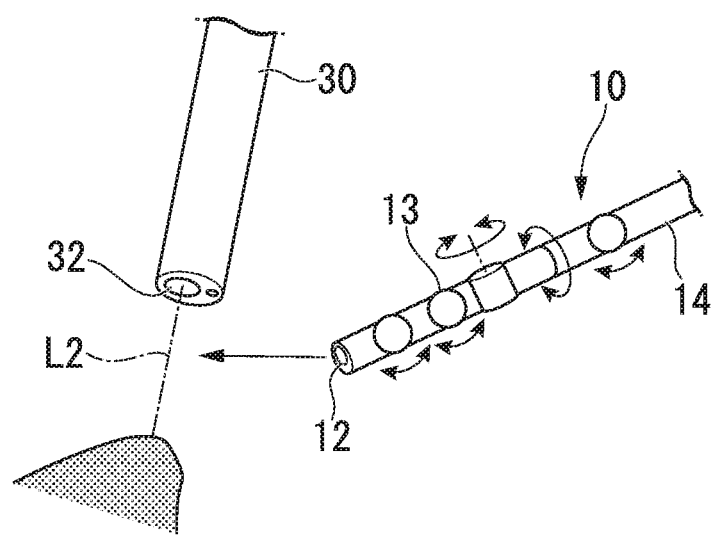
FIG. 4 is a view describing an action of the endoscope system.

When the endoscope system 1 is used, the first endoscope 10 and the second endoscope 30 are inserted into the body. That is, the insertion part 11 of the first endoscope 10 and the insertion part 31 of the second endoscope 30 are, for example, inserted into the body via a trocar and, as illustrated in FIG. 4, the imaging part 32 of the second endoscope 30 is guided to the vicinity of a treatment site in the body, and the imaging part 12 of the first endoscope 10 is guided to a position closer to the treatment site than the second endoscope 30 is, in the vicinity of the treatment site.

In a state in which both the imaging part 12 of the first endoscope 10 and the imaging part 32 of the second endoscope 30 are guided to the vicinity of the treatment site, a distance between the imaging part 12 of the first endoscope 10 and the treatment site is shorter than a distance between the imaging part 32 of the second endoscope 30 and the treatment site. Therefore, the imaging part 12 of the first endoscope 10 has a narrower imaging field-of-view than the imaging part 32 of the second endoscope 30. That is, in a case in which the first endoscope 10 and the second endoscope 30 are arranged in the body with the above distance relationship, the first endoscope 10 can capture a narrow-angle image including the treatment site, and the second endoscope 30 can capture a wide-angle image including the treatment site. Further, in the present embodiment, although the first endoscope 10 and the second endoscope 30 may have optical functions such as zooming and macro, description taking such optical functions into consideration will be omitted in the present specification.

After the first endoscope 10 and the second endoscope 30 are guided to the vicinity of the treatment site, for example, an operator (such as a surgeon and a scopist) observes the treatment site. First, to ascertain the treatment site in the body, the operator uses the second endoscope 30 and observes a wide area including the treatment site from a panoramic view. Here, the operator mainly operates the second endoscope 30. The operator grasps a situation in the vicinity of the treatment site by moving the operation part 34 of the second endoscope 30 and observing a desired site.

After grasping the situation of the treatment site, the operator holds the second endoscope 30 so that the treatment site is located at a field-of-view center of the image and makes an input to the field-of-view adjustment switch 40. Then, the drive control part 53 controls the arm 20 and the first endoscope 10 according to the control procedure from Step S1 to Step S4 above.

Figure 5:
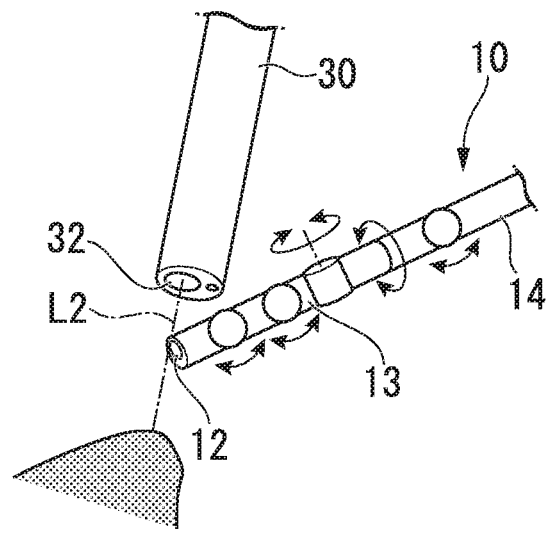
FIG. 5 is a view describing an action of the endoscope system.
Figure 7:
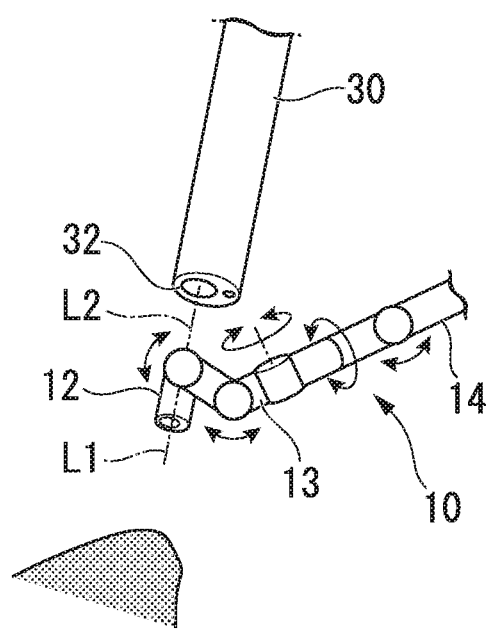
FIG. 7 is a view describing an action of the endoscope system.

Consequently, as illustrated in FIG. 5, the imaging part 12 of the first endoscope 10 enters the field of view of the second endoscope 30. Further, when the optical axis L1 of the imaging part 12 of the first endoscope 10 reaches an area within the circle C1 around the point X1 on the optical axis L2 of the second endoscope 30 as illustrated in FIG. 6, the movement of the imaging part 12 is stopped and then, the direction of the imaging part 12 of the first endoscope 10 is changed so that the optical axis L1 of the first endoscope 10 is coaxial with the optical axis L2 of the second endoscope 30 as illustrated in FIG. 7.

In a state in which the imaging part 12 of the first endoscope 10 is arranged so that the optical axis L1 of the first endoscope 10 is coaxial with the optical axis L2 of the second endoscope 30, the imaging part 12 of the first endoscope 10 is located at a field-of-view center of an image captured by the imaging part 32 of the second endoscope 30. The operator can grasp that the imaging part 12 of the first endoscope 10 is arranged in the vicinity of the treatment site from the wide-angle image captured by the imaging part 32 of the second endoscope 30. In the state in which the imaging part 12 of the first endoscope 10 is in the vicinity of the treatment site, the operator makes an input to the viewpoint change switch 39. Then, the image control part 52 of the control device 50 switches the image displayed on the main monitor 45 from the image captured by the imaging part 32 of the second endoscope 30 to the image captured by the imaging part 12 of the first endoscope 10.

Because the optical axis L1 of the first endoscope 10 and the optical axis L2 of the second endoscope L2 are coaxial with each other, a field-of-view center in the image captured by the imaging part 12 of the first endoscope 10 is coincident with a field-of-view center in the image captured by the imaging part 32 of the second endoscope 30. Because of this, by switching from the image captured by the imaging part 32 of the second endoscope 30 to the image captured by the first endoscope 10, an image in which a part including the field-of-view center of the wide-angle image is magnified (zoomed in) is displayed on the main monitor 45.

The image captured by the imaging part 12 of the first endoscope 10 is a narrow-angle image capturing the treatment site within the field of view. The operator can perform a treatment on the treatment site while looking at the image captured by the imaging part 12 of the first endoscope 10.

Further, as necessary, the operator can switch the image to be displayed on the main monitor 45 from the narrow-angle image captured by the imaging part 12 of the first endoscope 10 to the wide-angle image captured by the imaging part 32 of the second endoscope 30 by using the viewpoint change switch 39. This may be performed, for example, in a case in which a state of the surroundings of a treatment site is checked during treatment using a narrow-angle image. The imaging part 32 of the second endoscope 30 has a wide area including the imaging field of view of the first endoscope 10 as an imaging field of view. Because of this, when the image displayed on the main monitor 45 is switched from the image captured by the imaging part 12 of the first endoscope 10 to the image captured by the imaging part 32 of the second endoscope 30, an image in which the field of view of the narrow-angle image is made to wide-angle (zoomed out) is displayed on the main monitor 45.

The operator can observe surroundings of the treatment site by gripping and moving the operation part 34 of the second endoscope 30 in the state in which the image captured by the imaging part 32 of the second endoscope 30 is displayed on the main monitor 45. The first endoscope 10 is stopped in a state in which the first endoscope 10 can acquire a narrow-angle image capturing the treatment site at the field-of-view center.

In a case in which the observation of the surroundings of the treatment site using the second endoscope 30 is completed and the treatment on the treatment site is attempted to be resumed, the narrow-angle image including the treatment site is displayed again on the main monitor 45. In this case, first, the operator may easily restore the position of the field-of-view center of the imaging part 32 of the second endoscope 30 to the treatment site by referring to the position of the imaging part 12 of the first endoscope 10 based on the image captured by the imaging part 32 of the second endoscope 30. After the operator substantially returns the position of the field-of-view center of the imaging part 32 of the second endoscope 30 to the treatment site, the operator makes an input to the viewpoint change switch 39 and switches the image displayed on the main monitor 45 from the image captured by the imaging part 32 of the second endoscope 30 to the image captured by the imaging part 12 of the first endoscope 10.

The first endoscope 10 is stopped in a state in which the first endoscope 10 can acquire a narrow-angle image capturing the treatment site at the field-of-view center. That is, the first endoscope 10 maintains the positional relationship before switching from the narrow-angle image to the wide-angle image. Because of this, the operator may easily resume the treatment after the image displayed on the main monitor 45 is switched from the wide-angle image to the narrow-angle image.

When the entire tissue including the treatment site is moved during observation using the second endoscope 30, the positional relationship between the treatment site and the first endoscope 10 is changed, and the position or orientation of the treatment site in the image captured by the imaging part 12 of the first endoscope 10 changes in some cases. In this case, in the state in which the treatment site is captured at the field-of-view center of the imaging part 32 of the second endoscope 30, the operator may move the imaging part 12 of the first endoscope 10 to the treatment site by making an input to the field-of-view adjustment switch 40. Here, as the drive control part 53 controls the arm 20 and the first endoscope 10 according to the control procedure from Step S1 to Step S4 above, the optical axis L2 of the imaging part 32 of the second endoscope 30 and the optical axis L1 of the imaging part 12 of the first endoscope 10 become coaxial with each other. By making an input to the viewpoint change switch 39 in this state, a narrow-angle image capturing the treatment site at the field-of-view center is displayed on the main monitor 45, and a treatment on the new site can be performed.

As a result of observing the surroundings of the treatment site by gripping and moving the operation part 34 of the second endoscope 30, the operator may have to perform another treatment with a new site as a treatment site in some cases. In a case in which a new site is set as a treatment site, in the state in which the new site, which is the treatment site, is captured at the field-of-view center of the imaging part 32 of the second endoscope 30, the operator may move the imaging part 12 of the first endoscope 10 to the new site by making an input to the field-of-view adjustment switch 40. Here, as the drive control part 53 controls the arm 20 and the first endoscope 10 according to the control procedure from Step S1 to Step S4 above, the optical axis L2 of the imaging part 32 of the second endoscope 30 and the optical axis L1 of the imaging part 12 of the first endoscope 10 become coaxial with each other. By making an input to the viewpoint change switch 39 in this state, a narrow-angle image capturing the new site as the treatment site at the field-of-view center is displayed on the main monitor 45, and a treatment on the new site can be performed.

As an example, a surgeon performing a treatment using the endoscope system 1 according to the present embodiment may perform a treatment while looking at a wide-angle image and a narrow-angle image including a treatment site by using the main monitor 45. Further, a scopist operating the first endoscope 10 and the second endoscope 30 of the endoscope system 1 according to the present embodiment may adjust the position or orientation of each of the endoscopes independently of the treatment by the surgeon or in cooperation with the treatment by the surgeon by using the first sub-monitor 26 and the second sub-monitor 37.

As described above, in the present embodiment, because the optical axes of the two endoscopes (the first endoscope 10 and the second endoscope 30) are coaxial with each other and respectively capture a narrow-angle image and a wide-angle image, when an image displayed on the main monitor 45 on the basis of an input to the viewpoint change switch 39 is switched by the image control part 52, an operational feeling such as zoom out for a narrow-angle image and zoom in for a wide-angle image may be obtained. In the endoscope system 1 according to the present embodiment, because most of the operations for making the optical axes of the two endoscopes coincident with each other can be automated, the burden on the operator is reduced.

Further, in a case in which a treatment is performed using a single endoscope in conventional laparoscopic surgery, states of surrounding tissues need to be checked or running of blood vessels being currently treated needs to be checked in some cases while a treatment such as a separation operation or exposing blood vessel is performed in a close field of view (narrow-angle field of view).

In this case, by keeping the endoscope which is brought close to the treatment site away and performing observation from a position at which the entire treatment site can be seen, a task in which surrounding tissues or running of blood vessels is checked and then the endoscope is returned to its original position is performed. The initial close field of view is a surgical field (field of view) created by a surgeon giving an instruction to a scopist to have a state in which it is easy to perform a treatment. However, by observing the entire treatment site, the field of view that is initially created is destroyed. After observing the entire treatment site, because the surgeon has to repeat giving an instruction to the scopist to reproduce the state (field of view) in which it is easy to perform the treatment, the time until the surgeon can return to performing the treatment becomes long, and the surgeon may feel stress and fatigue. Because of this, to avoid such stress and fatigue, the surgeon may want to avoid destroying the field of view with a small degree of checking, and there is a possibility that the surgeon may give up checking the entire treatment site despite wishing to do so.

In the present embodiment, the surgeon can check the surroundings of the treatment site in a wide-angle field of view at a moment when the surgeon wants to do so, and after the checking, the surgeon can promptly return to a field of view in which the treatment was being performed. Because of this, in the present embodiment, there is little time lag before returning to performing the treatment, and the surgeon may feel less stress and fatigue. Further, in the present embodiment, because surrounding tissues can be appropriately checked using a wide-angle image, there is a possibility that safer surgery may be able to be performed.

Second Embodiment

Figure 8:
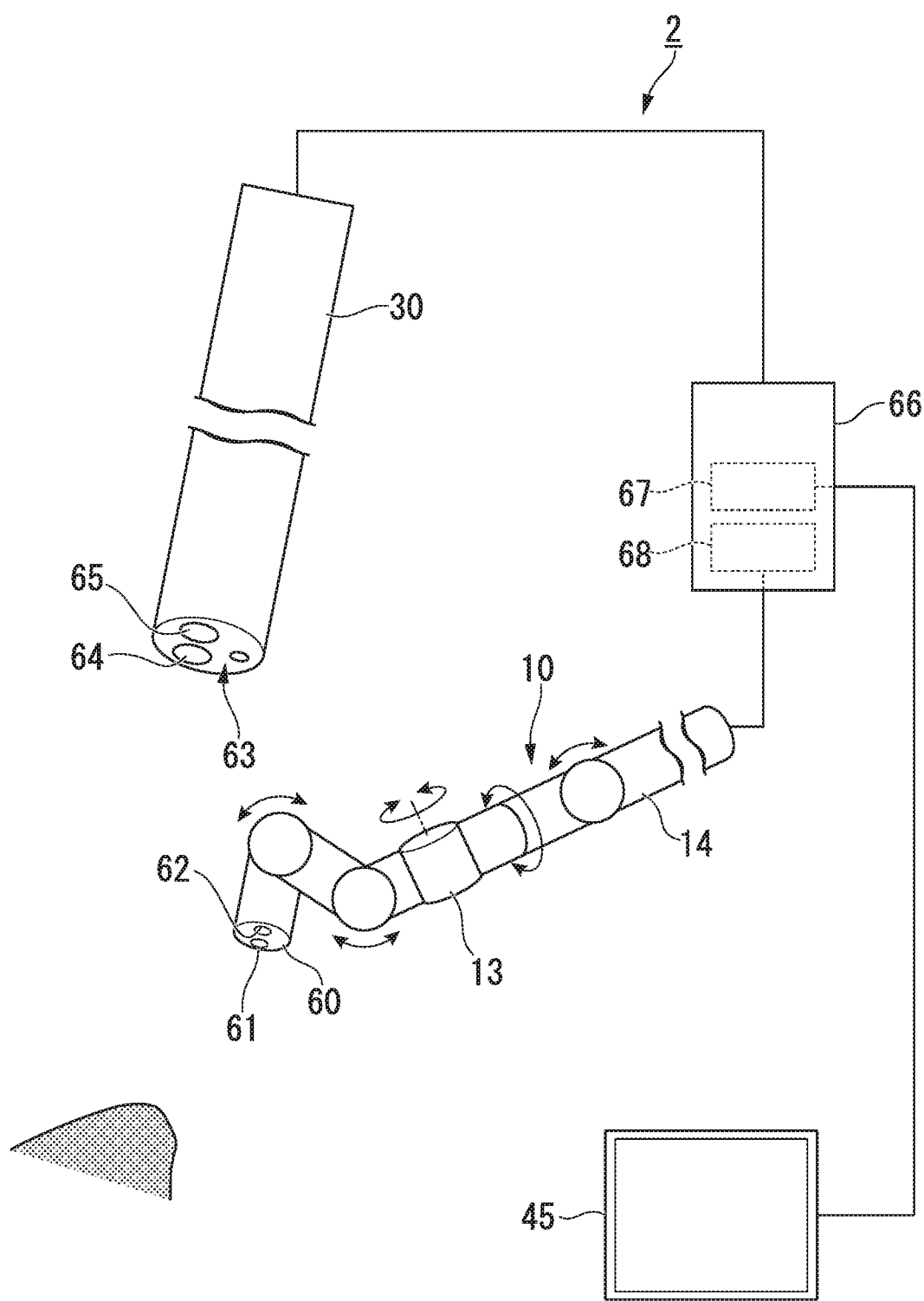
FIG. 8 is a schematic view illustrating a part of an endoscope system according to a second embodiment of the present invention.
Figure 9:
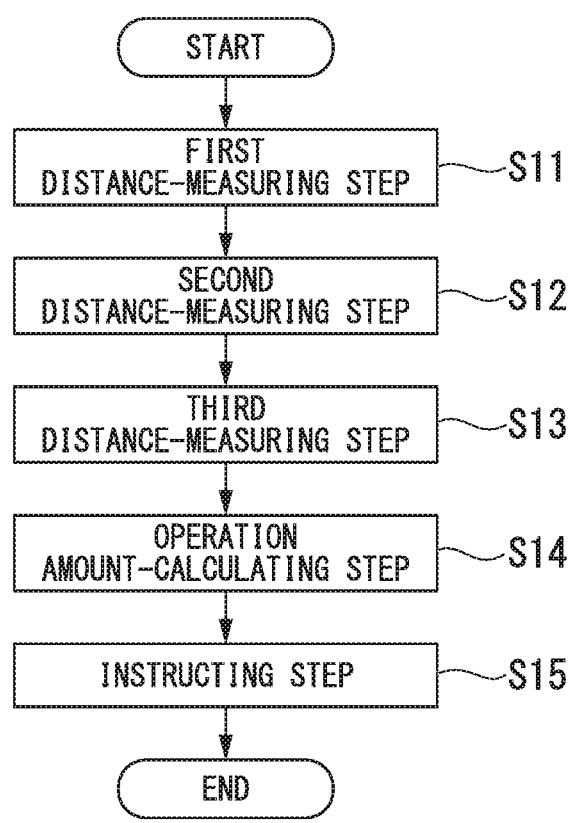
FIG. 9 is a flowchart illustrating a control procedure by a control device of the endoscope system.

A second embodiment of the present invention will be described. In the present embodiment, like reference numerals as those in the first embodiment will be given to elements the same as those in the first embodiment, and overlapping descriptions will be omitted. FIG. 8 is a schematic view illustrating a part of an endoscope system according to the second embodiment of the present invention. FIG. 9 is a flowchart illustrating a control procedure by a control device of the endoscope system.

An endoscope system 2 according to the present embodiment, which is partly illustrated in FIG. 8, includes a distance measurer for measuring a distance to an imaging target site provided in the first endoscope 10, the second endoscope 30, and a control device 66 (also referenced throughout this disclosure as controller). The control device 66 can be realized by hardware such as one or more Central Processing Unit (CPU), and by reading instructions stored on a computer readable storage device.

As a specific example, the first endoscope 10 according to the present embodiment includes, instead of the imaging part 12 of the first embodiment, an imaging part 60 having a constitution different from that of the imaging part 12 disclosed in the first embodiment. The second endoscope 30 according to the present embodiment includes, instead of the imaging part 32 of the first embodiment, an imaging part 63 having a constitution different from that of the imaging part 32 disclosed in the first embodiment.

Further, the endoscope system 2 according to the present embodiment includes, instead of the control device 50 of the first embodiment, a control device 66 that includes, in an operation procedure, a step of operating the first endoscope 10 and the arm 20 (see FIG. 1) in consideration of a distance to an imaging target on the basis of images respectively captured by the imaging parts 60 and 63 of the present embodiment.

The imaging part 60 of the first endoscope 10 has a different constitution from the imaging part 12 of the first endoscope 10 disclosed in the first embodiment in that the imaging part 60 can acquire three-dimensional information on an imaging target site. As a specific example, the first endoscope 10 includes a left-side imaging part 61 and a right-side imaging part 62.

The left-side imaging part 61 and the right-side imaging part 62 capture a set of two images having parallax with respect to the same imaging target site. For example, each of the left-side imaging part 61 and the right-side imaging part 62 may have an image sensor and an objective optical system independently. An image captured by the left-side imaging part 61 and an image captured by the right-side imaging part 62 are transmitted to an image control part 67 of the control device 66 via a signal line (not illustrated) as in the first embodiment.

The imaging part 63 of the second endoscope 30 includes, for example, a left-side imaging part 64 and a right-side imaging part 65 like the imaging part 60 of the first endoscope 10.

The image control part 67 of the control device 66 has a function of measuring a distance from the first endoscope 10 to an imaging target site on the basis of images respectively acquired by the left-side imaging part 61 and the right-side imaging part 62 of the first endoscope 10. As an example, the image control part 67 of the control device 66 measures a distance to the imaging target site using the parallax of images acquired by the left-side imaging part 61 and the right-side imaging part 62 of the first endoscope 10.

The image control part 67 of the control device 66 has a function of measuring a distance from the second endoscope 30 to an imaging target site on the basis of images respectively acquired by the left-side imaging part 64 and the right-side imaging part 65 of the second endoscope 30. As an example, the image control part 67 of the control device 66 measures a distance to the imaging target site using the parallax of images acquired by the left-side imaging part 64 and the right-side imaging part 65 of the second endoscope 30.

The constitution for measuring a distance between the first endoscope 10 and an imaging target site thereof or a distance between the second endoscope 30 and an imaging target site thereof is not limited to the above constitution. For example, the first endoscope 10 or the second endoscope 30 may have an appropriate constitution such as a known laser distance-measuring device or infrared distance-measuring device.

An example of specific control by the control device 66 of the present embodiment for moving the first endoscope 10 and the arm 20 will be mainly described with respect to differences from the control procedure in the first embodiment.

In the present embodiment, the control device 66 includes the steps from Step S1 to Step S4 disclosed in the first embodiment in a control procedure. Because of this, in a state in which both the first endoscope 10 and the second endoscope 30 capture a treatment site at a field-of-view center, the endoscope system 2 according to the present embodiment may capture a narrow-angle image and a wide-angle image in a positional relationship in which optical axes thereof coincide with each other and may display any one or both of the narrow-angle image and the wide-angle image on the main monitor 45.

Further, in the present embodiment, in the state in which both the first endoscope 10 and the second endoscope 30 capture an image capturing a treatment site at a field-of-view center, a control procedure (see FIG. 9) in a case in which the control device 66 operates the first endoscope 10 and the arm 20 by following movement of the second endoscope 30 is different from the first embodiment.

In the state in which both the first endoscope 10 and the second endoscope 30 capture an image including a treatment site at a field-of-view center, the control device 66 measures a distance between an imaging target site of the first endoscope 10 and the first endoscope 10. For example, the control device 66 calculates a distance from coordinates of a position of an optical axis of the imaging part 60 of the first endoscope 10 in the reference coordinate system to a field-of-view center of one predetermined image of the set of two images captured by the imaging part 60 of the first endoscope 10 (a first distance-measuring step, Step S11, see FIG. 9).

The control device 66 measures a distance between an imaging target site of the second endoscope 30 and the second endoscope 30. For example, the control device 66 calculates a distance from coordinates of a position of an optical axis of the imaging part 63 of the second endoscope 30 in the reference coordinate system to a field-of-view center of one predetermined image of the set of two images captured by the imaging part 63 of the second endoscope 30 (a second distance-measuring step, Step S12, see FIG. 9). Step S12 may be performed before Step S11 or performed after Step S11.

In Step S11 and S12, both the first endoscope 10 and the second endoscope 30 capture a treatment site at a field-of-view center, and distances calculated by Step S11 and Step S12 are a distance between the first endoscope 10 and the treatment site and a distance between the second endoscope 30 and the treatment site, respectively.

In a case in which an operator moves the second endoscope 30 and starts a treatment with a new site as a treatment site, the operator operates the second endoscope 30 so that the field-of-view center of the image captured by the imaging part 63 of the second endoscope 30 is adjusted to the new site, which is the treatment site. Then, the operator makes an input to the field-of-view adjustment switch 40.

When the control device 66 detects that there is an input from the field-of-view adjustment switch 40, the control device 66 first calculates a distance between a field-of-view center of an image captured by the imaging part 63 of the second endoscope 30 and the second endoscope 30 (a third distance-measuring step, Step S13, see FIG. 9). In Step S13, the control device 66 detects the position and orientation of the optical axis L2 of the second endoscope 30 as in the first embodiment.

In Step S13, the new treatment site is located at the field-of-view center of the image captured by the imaging part 63 of the second endoscope 30. Because of this, in Step S13, a distance between the second endoscope 30 and the new treatment site is calculated.

After Step S13, a drive control part 68 of the control device 66 calculates an operation amount for operating the first endoscope 10 and the arm 20 such that the first endoscope 10 and the arm 20 approach the position and orientation of the optical axis L2 of the second endoscope 30 recognized in Step S13 (Step S14, see FIG. 9).

In Step S14, the drive control part 68 sets a position deviated by a predetermined distance toward a front side in an optical axis direction from coordinates indicating the position of the optical axis L2 of the second endoscope 30 as a movement target position of the optical axis L1 of the first endoscope 10.

In a case in which the distance between the second endoscope 30 and the imaging target site thereof is shorter than the distance between the first endoscope 10 and the imaging target site thereof, the control device 66 causes, for example, the main monitor 45 to display a message prompting movement of the first endoscope 10 or the second endoscope 30 so that the second endoscope 30 is separated from the imaging target site thereof. In this case, the control device 66 returns to Step S12, recalculates the distance between the second endoscope 30 and the imaging target site thereof, and sets the position deviated by the predetermined distance toward the front side in the optical axis direction from the coordinates indicating the position of the optical axis L2 of the second endoscope 30 as the movement target position of the optical axis L1 of the first endoscope 10.

In this way, in Step S14, the control device 66 sets the movement target position of the optical axis L1 of the first endoscope 10 in an area between a distal end and the imaging target site of the imaging part 63 of the second endoscope 30.

Further, the drive control part 68 of the control device 66 sets a movement path from a current position of the optical axis L1 of the first endoscope 10 to the movement target position. A method of setting the movement path from the current position of the optical axis L1 of the first endoscope 10 to the movement target position takes into consideration that there is no obstacle in the movement path. The movement path set in Step S14 may be set using the same setting method as the movement path set in Step S3 in the first embodiment. After the movement path of the optical axis L1 of the first endoscope 10 is set, the drive control part 68 calculates an operation amount of the arm 20 for moving the first endoscope 10 so that the optical axis moves along the movement path.

In Step S14, the drive control part 68 sets an operation target direction of the imaging part 60 of the first endoscope 10 so that a direction of the optical axis L1 of the first endoscope 10 is made to coincide with a direction of the optical axis L2 of the second endoscope 30. In the present embodiment, in Step S14, the drive control part 68 calculates an operation amount of the joint part 13 for rotating the imaging part 60 of the first endoscope 10 around coordinates indicating the position of the optical axis L1 of the first endoscope 10 so that a direction of the optical axis L1 of the first endoscope 10 when the optical axis L1 of the first endoscope 10 is located at the movement target position is parallel to a direction of the optical axis L2 of the second endoscope 30.

In this way, in Step S14, the drive control part 68 calculates the operation amount of the arm 20 and the operation amount of the joint part 13.

This completes Step S14, and the procedure proceeds to Step S15.

Step S15 is an instructing step of outputting operation instructions for operating the arm 20 and the joint part 13 on the basis of the operation amount of the arm 20 and the operation amount of the joint part 13 calculated in Step S14 above to the arm 20 and the joint part 13 (see FIG. 9).

In Step S15, the drive control part 68 operates the arm 20 and the joint part 13 by outputting operation instructions to the arm 20 and the joint part 13. For example, in Step S15, the drive control part 68 first outputs an operation instruction to the arm 20, thereby moving the first endoscope 10 until the position of the optical axis L1 of the first endoscope 10 reaches the movement target position on the optical axis L2 of the second endoscope 30. Then, the drive control part 68 outputs an operation instruction to the joint part 13, thereby rotating the imaging part 60 of the first endoscope 10 on the optical axis L2 of the second endoscope 30 until the optical axis L1 of the first endoscope 10 is coaxial with the optical axis L2 of the second endoscope 30.

This completes Step S15. In this way, by the operation procedure from Step S11 to Step S15 above, the drive control part 68 operates the first endoscope 10 and the arm 20 until the optical axis L1 of the first endoscope 10 and the optical axis L2 of the second endoscope 30 become coaxial with each other corresponding to the input to the field-of-view adjustment switch 40. Further, in the present embodiment, the distance between the first endoscope 10 and the treatment site before the operations of the first endoscope 10 and the arm 20 and the distance between the first endoscope 10 and the new treatment site after the operations of the first endoscope 10 and the arm 20 are equal to each other. Because of this, in a case in which a new treatment is performed using an image captured by the imaging part 60 of the first endoscope 10, it is easy to grasp a situation of a treatment site thereof.

Modified Example

A modified example of the above embodiment will be described.

In the endoscope system 2 of the present modified example, in the movement path for moving the imaging part 60 of the first endoscope 10 from a certain treatment site (first site) to another new treatment site (second site), the imaging part 60 of the first endoscope 10 can be moved while a distance to a tissue or the like including the treatment site is kept constant.

As a specific example, in the endoscope system 2 of the present modified example, in Step S14 in the above second embodiment, the drive control part 68 sets the movement path of the optical axis L1 of the first endoscope 10 so that a distance between a line connecting the first site to the second site by, for example, the shortest path, and the position of the optical axis L1 of the first endoscope 10 is always the same on the basis of an image captured by the imaging part 60 of the first endoscope 10.

In the present modified example, in a case in which there is an obstacle having irregularities on a line connecting a first site and a second site of a tissue, the imaging part 60 of the first endoscope 10 may move while avoiding the obstacle having irregularities corresponding to the obstacle having irregularities.

Instead of the constitution of the present modified example, the drive control part 68 may recognize an obstacle having irregularities on a line connecting a first site and a second site of a tissue on the basis of an image from the imaging part 60 of the first endoscope 10 and may move the first endoscope 10 while avoiding the obstacle having irregularities. In this case, the drive control part 68 calculates a distance between the first endoscope 10 and the tissue while appropriately adjusting the direction of the imaging part 60 in a process in which the first endoscope 10 moves, thereby moving the first endoscope 10 while the distance between the first endoscope 10 and the tissue is kept constant.

Third Embodiment

Figure 10:
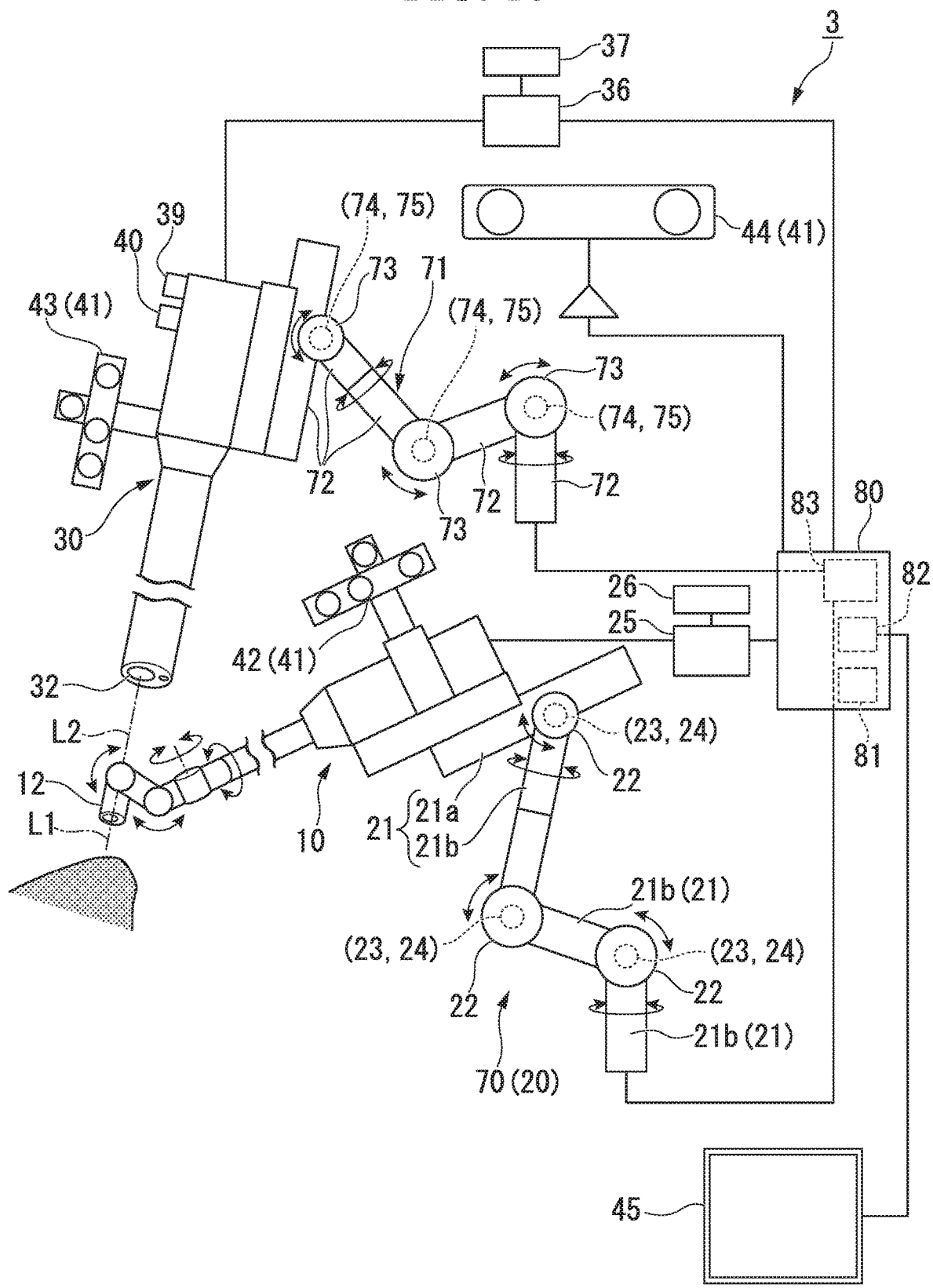
FIG. 10 is a schematic overall view illustrating an endoscope system according to a third embodiment of the present invention.
Figure 11:
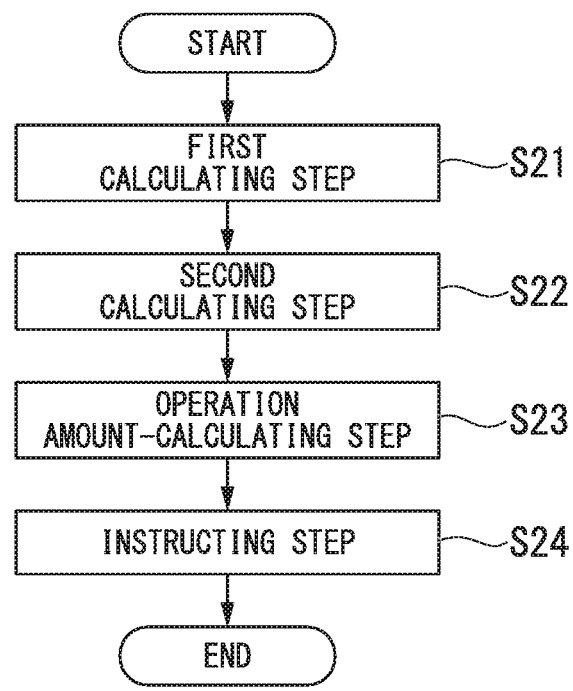
FIG. 11 is a flowchart illustrating a control procedure by a control device of the endoscope system.

A third embodiment of the present invention will be described. In the present embodiment, like reference numerals as in the above embodiments will be given to elements the same as those in the above embodiments, and overlapping descriptions will be omitted. FIG. 10 is a schematic overall view illustrating an endoscope system according to the present embodiment. FIG. 11 is a flowchart illustrating a control procedure by a control device 80 of the endoscope system.

An endoscope system 3 according to the present embodiment illustrated in FIG. 10 has a different constitution from the endoscope system 1 according to the first embodiment in that the endoscope system 3 includes an arm (a second arm 71) for moving the second endoscope 30.

That is, the endoscope system 3 according to the present embodiment includes the first endoscope 10 and the second endoscope 30 disclosed in the first embodiment, a first arm 70 for moving the first endoscope 10, the second arm 71 for moving the second endoscope 30, and the control device 80 (also referenced throughout this disclosure as controller). The control device 80 can be realized by hardware such as one or more Central Processing Unit (CPU), and by reading instructions stored on a computer readable storage device.

Constitutions of the first endoscope 10 and the second endoscope 30 are the same as in the first embodiment. Further, the first endoscope 10 and the second endoscope 30 in the present embodiment may be of the same type having the same constitution.

The first arm 70 has the same constitution as the arm 20 disclosed in the first embodiment.

The second arm 71 has the same constitution as the arm 20 disclosed in the first embodiment. That is, the second arm 71 has link parts 72, joint parts 73, actuators 74, and encoders 75. The operation part 34 of the second endoscope 30 may be attached to the link part 72 of the second arm 71. The second arm 71 may be connected to the control device 80.

The control device 80 included in the endoscope system 3 according to the present embodiment controls operations of the first endoscope 10, the second endoscope 30, the first arm 70, and the second arm 71.

The control device 80 includes a position calculation part 81, an image control part 82, and a drive control part 83 capable of outputting operation instructions for operating the first endoscope 10 and the first arm 70 in the same manner as in the first embodiment to the first endoscope 10 and the first arm 70.

The drive control part 83 of the present embodiment outputs an operation instruction for operating the second arm 71 to the second arm 71. In the present embodiment, in a case in which the second endoscope 30 has a joint part the same as the joint part 13 of the first endoscope 10, the drive control part 83 may be configured to control the joint part provided in the second endoscope 30.

Next, a constitution of the control device 80 will be described by showing a control procedure of a main part in the endoscope system 3 according to the present embodiment with reference to FIG. 11.

Unlike the control device 50 disclosed in the first embodiment, the control device 80 of the endoscope system 3 according to the present embodiment has a control procedure for operating the second arm 71.

That is, in a state in which the first endoscope 10 is capturing a narrow-angle image including a treatment site, the control device 80 moves the second endoscope 30 by operating the second arm 71 so that the optical axis L1 of the imaging part 12 of the first endoscope 10 and the optical axis L2 of the imaging part 32 of the second endoscope 30 are coaxial.

The control procedure for moving the second endoscope 30 includes the following steps from Step S21 to Step S24.

First, the control device 80 recognizes the position and orientation of the optical axis L1 of the first endoscope 10 on the basis of an image including the first marker 42 captured by the camera 44 of the position-and-orientation-detecting device 41 (a first calculating step, Step S21, see FIG. 11).

Further, the control device 80 recognizes the position and orientation of the second endoscope 30 on the basis of an image including the second marker 43 captured by the camera 44 of the position-and-orientation-detecting device 41 (a second calculating step, Step S22, see FIG. 11). Step S22 may be performed before Step S21 or performed after Step S21.

After Step S22, the drive control part 83 of the control device 80 calculates an operation amount of the second endoscope 30 so that the optical axis L1 of the imaging part 12 of the first endoscope 10 and the optical axis L2 of the imaging part 32 of the second endoscope 30 are coaxial (an operation amount-calculating step, Step S23, see FIG. 11). As an example, in Step S23, the drive control part 83 of the control device 80 calculates a movement amount of the second endoscope 30 so that the position and direction of the optical axis L2 of the second endoscope 30 pass through the position of the optical axis L1 of the first endoscope 10 in the reference coordinate system and are parallel to a direction of the optical axis. The movement amount of the second endoscope 30 in Step S23 calculates an operation amount of the second arm 71 to which the second endoscope 30 is attached.

This completes Step S23, and the procedure proceeds to Step S24.

Step S24 is an instructing step of outputting an operation instruction for operating the second arm 71 on the basis of the operation amount calculated in Step S23 above to the second arm 71 (see FIG. 11).

In Step S24, the operation amount calculated in Step S23 is converted into an operation amount of each of the joint parts 22 of the second arm 71 and is output as an operation instruction to the actuators 23 respectively provided in the joint parts 22 of the second arm 71. Consequently, the second arm 71 operates in accordance with the operation instruction output in Step S24, and the second arm 71 moves the second endoscope 30.

By the drive control part 83 operating the second arm 71 in accordance with the control procedure including the steps from Step S21 to Step S24, the control device 80 may operate the second endoscope 30 following the operation of the first endoscope 10 so that the optical axis L2 of the imaging part 32 of the second endoscope 30 is coaxial with the optical axis L1 of the imaging part 12 of the first endoscope 10.

Next, a control procedure in which the control device 80 sets a main-sub relationship between the first endoscope 10 and the second endoscope 30 will be described.

The control device 80 of the present embodiment sets any one of the first endoscope 10 and the second endoscope 30 as a master and sets the other one of the first endoscope 10 and the second endoscope 30 that is not set as the master as a slave. The endoscope from the first endoscope 10 and the second endoscope 30 set as the master is an endoscope operated by an operator, and the endoscope from the first endoscope 10 and the second endoscope 30 set as the slave is automatically controlled by the control device 80 to move by following the movement of the optical axis L1 of the imaging part 12 of the endoscope set as the master.

The main-sub relationship between the first endoscope 10 and the second endoscope 30 is set on the basis of a state of an input to the viewpoint change switch 39. That is, in a case in which an input for making an image displayed on the main monitor 45 be an image from the first endoscope 10 is made to the viewpoint change switch 39, the control device 80 sets the first endoscope 10 as a main endoscope and sets the second endoscope 30 as a sub endoscope. Conversely, in a case in which an input for making an image displayed on the main monitor 45 be an image from the second endoscope 30 is made to the viewpoint change switch 39, the control device 80 sets the second endoscope 30 as a main endoscope and sets the first endoscope 10 as a sub endoscope. In this way, the control device 80 sets the main-sub relationship between the first endoscope 10 and the second endoscope 30 on the basis of a state of an input to the viewpoint change switch 39.

The control procedure by the control device 80 in the endoscope system 3 according to the present embodiment will be described in more detail together with an overall operation of the endoscope system 3.

In the endoscope system 3 according to the present embodiment, as in the first embodiment described above, the imaging part 12 of the first endoscope 10 may be moved so that the optical axis L1 of the first endoscope 10 is coaxial with the optical axis L2 of the second endoscope 30. That is, the second endoscope 30 that captures a wide-angle image to observe a treatment site from a panoramic view is set as a main endoscope, and the first endoscope 10, which is a sub endoscope, is automatically controlled by the control device 80 to follow the operation of the second endoscope 30 to be coaxial with the optical axis L2 of the imaging part 32 of the second endoscope 30, which is the main endoscope.

Further, in the present embodiment, when the entire first endoscope 10 or the joint part 13 of the first endoscope 10 is operated in a state in which a narrow-angle image from the imaging part 12 of the first endoscope 10 is displayed on the main monitor 45, the imaging part 12 of the first endoscope 10, which is a main endoscope, moves, and the second endoscope 30, which is a sub endoscope, moves by following the movement of the imaging part 12 of the first endoscope 10.

For example, in a state in which a narrow-angle image of a treatment site is captured using the first endoscope 10 and the narrow-angle image is displayed on the main monitor 45, the position and orientation of the second endoscope 30 is controlled by the control device 80 so that the optical axis L2 of the imaging part 32 of the second endoscope 30 is coaxial with the optical axis L1 of the imaging part 12 of the first endoscope 10. Therefore, in a case in which the operator makes an input to the viewpoint change switch 39 and switches an image displayed on the main monitor 45 by the image control part 82 from a narrow-angle image to a wide-angle image, the wide-angle image displayed on the main monitor 45 is an image in which a field-of-view center of the narrow-angle image is captured at a field-of-view center thereof. Because of this, when the image displayed on the main monitor 45 is switched from an image captured by the imaging part 12 of the first endoscope 10 to an image captured by the imaging part 32 of the second endoscope 30 by the image control part 82, an image in which the field of view of the narrow-angle image is made to wide-angle (zoomed out) is displayed on the main monitor 45.

In the present embodiment, in the state in which an image captured by the imaging part 32 of the second endoscope 30 is displayed on the main monitor 45, the control device 80 sets the second endoscope 30 as a main endoscope and sets the first endoscope 10 as a sub endoscope. Further, in the state in which the image captured by the imaging part 32 of the second endoscope 30 is displayed on the main monitor 45, the control device 80 releases interlocking between movement of the second endoscope 30 and movement of the first endoscope 10 until there is an input to the field-of-view adjustment switch 40. That is, in the state in which the image captured by the imaging part 32 of the second endoscope 30 is displayed on the main monitor 45, the operator can observe a state of the surroundings of the treatment site by moving the second endoscope 30 while the imaging part 12 of the first endoscope 10 is stopped.

In a case in which the observation of the state of the surroundings of the treatment site is completed and the treatment on the treatment site is resumed, the operator makes an input to the viewpoint change switch 39 and switches the image displayed on the main monitor 45. In this case, a main endoscope is switched from the second endoscope 30 to the first endoscope 10, and a sub endoscope is switched from the first endoscope 10 to the second endoscope 30. As a result, the second endoscope 30, which is the sub endoscope, is automatically controlled by the control device 80. Specifically, as in the steps from Step S21 to Step S24 in the present embodiment, the second arm 71 is controlled by the control device 80 so that the optical axis L2 of the imaging part 32 of the second endoscope 30 is coaxial with the optical axis L1 of the imaging part 32 of the first endoscope 10.

In the present embodiment, in the state in which an image captured by the imaging part 12 of the first endoscope 10 is displayed on the main monitor 45, the operator may resume a treatment while looking at the narrow-angle image including the treatment site even when the second arm 71 is being operated by the control device 80. That is, an operation in which the second endoscope 30 is operated to observe a state of the surroundings of the treatment site and then the second endoscope 30 is returned to its original state is automatically controlled by the control device 80 in the background after the image displayed on the main monitor 45 is switched.

Because of this, the operator does not need to manually move the second endoscope 30 to return the second endoscope 30 to its original state, and because the optical axis L2 of the second endoscope 30 automatically returns to a state of being coaxial with the optical axis L1 of the first endoscope 10, field-of-view centers of the narrow-angle image and the wide-angle image coincide with each other in a case in which the wide-angle image is captured again.

Further, in a case in which the observation of the state of the surroundings of the treatment site is completed and a site different from the treatment site is set as a new treatment site, the operator makes an input to the field-of-view adjustment switch 40. In this case, a main endoscope is the second endoscope 30, and the first endoscope 10, which is a sub endoscope, is automatically controlled by the control device 80. Specifically, as in the steps from Step S1 to Step S4 in the first embodiment, the first arm 70 or the joint part 13 is controlled by the control device 80 so that the optical axis L1 of the imaging part 12 of the first endoscope 10 is coaxial with the optical axis L2 of the imaging part 32 of the second endoscope 30.

As described above, in the present embodiment, while the operator, for example, observes the treatment site in a desired direction by moving the imaging part 12 of the first endoscope 10, the control device 80 may move the second endoscope 30 to follow movement of the imaging part 12 of the first endoscope 10. As a result, according to the endoscope system 3 according to the present embodiment, a state in which deviation between the field-of-view centers of the imaging part 12 of the first endoscope 10 and the field-of-view center of the imaging part 32 of the second endoscope 30 is always eliminated may be set.

Further, in a case in which a treatment on a treatment site is resumed after the surroundings of the treatment site are observed from a panoramic view using a wide-angle image from the second endoscope 30, the control device 80 returns the position of the second endoscope 30 to its original position and orientation by automatic control. That is, because the operation of moving the second endoscope 30 so that the second endoscope 30 captures the original treatment site at the field-of-view center is performed by the control device 80 instead of the operator, the operational burden on the operator can be reduced.

Modified Example

A modified example of the present embodiment will be described.

In the endoscope system 3 of the present modified example, a part of the control procedure for moving the second endoscope 30 by following the movement of the imaging part 12 of the first endoscope 10 is different from the above embodiment.

That is, in the present modified example, when the operator makes an input to the field-of-view adjustment switch 40, the control device 80 operates the second arm 71 so that the optical axis L2 of the imaging part 32 of the second endoscope 30 is coaxial with the optical axis L1 of the imaging part 12 of the first endoscope 10. As an example, Step S21 and Step S22 described above may be started with the control device 80 detecting that the operator made an input to the field-of-view adjustment switch 40 as a trigger.

In the endoscope system 3 of the present modified example, in a case in which the imaging part 12 of the first endoscope 10 is moved, the second endoscope 30 does not move until the operator makes an input to the field-of-view adjustment switch 40.

For example, in a state in which only the narrow-angle image from the first endoscope 10 is displayed on the main monitor 45 while a treatment site is being captured using the imaging part 12 of the first endoscope 10, in what orientation the second endoscope 30 is in the body cannot be grasped in some cases, and there is a situation in which it is not preferable to automatically move the second endoscope 30 in the body at all times.

In the present modified example, the drive control part 83 of the control device 80 may control the second arm 71 to prohibit an operation of the second arm 71 moving the second endoscope 30 in a case in which there is no input to the field-of-view adjustment switch 40, thereby making the second arm 71 operable only when it is necessary to move the second endoscope 30 by the second arm 71.

Modified Example

A modified example of the present embodiment will be described.

In the endoscope system 3 of the present modified example, a part of the control procedure for moving the second endoscope 30 by following the movement of the imaging part 12 of the first endoscope 10 is different from the above embodiment.

In the present modified example, the drive control part 83 of the control device 80 operates the second arm 71 so that, when the optical axis L1 of the imaging part 12 of the first endoscope 10 and the optical axis L2 of the imaging part 32 of the second endoscope 30 are spaced apart by a predetermined distance or more, the optical axis L2 of the imaging part 32 of the second endoscope 30 is coaxial with the optical axis L1 of the imaging part 12 of the first endoscope 10. As an example, Step S21 and Step S22 described above may be started with the drive control part 83 detecting, via the position calculation part 81, that the optical axis L1 of the imaging part 12 of the first endoscope 10 and the optical axis L2 of the imaging part 32 of the second endoscope 30 are spaced apart by a predetermined distance or more as a trigger.

The distance between the optical axis L1 of the imaging part 12 of the first endoscope 10 and the optical axis L2 of the imaging part 32 of the second endoscope 30 is, for example, calculated by the position calculation part 81 or the drive control part 83 on the basis of the position and orientation of the first endoscope 10 and the position and orientation of second endoscope 30 in the reference coordinate system.

In the endoscope system 3 of the present modified example, in a case in which the imaging part 12 of the first endoscope 10 is moved, the second endoscope 30 does not move until the optical axis L1 of the imaging part 12 of the first endoscope 10 and the optical axis L2 of the imaging part 32 of the second endoscope 30 are spaced apart by a predetermined distance or more. That is, the control device 80 moves the second endoscope 30 only in a case in which there is a deviation of a predetermined threshold value or larger between the optical axis L1 of the imaging part 12 of the first endoscope 10 and the optical axis L2 of the imaging part 32 of the second endoscope 30. For example, the control device 80 may calculate a total sum of the deviations accumulated from the time of the closest movement of the second endoscope 30 to the present as a movement amount to which the second endoscope 30 is to be moved. The control device 80 does not move the second endoscope 30 in a case in which the movement amount calculated on the basis of the total sum of deviations does not exceed the predetermined threshold value, and moves the second endoscope 30 to reduce deviation when the movement amount calculated on the basis of the total sum of deviations exceeds the predetermined threshold value. Because of this, at the time of fine operation when capturing a treatment site using the first endoscope 10, the second endoscope 30 may be used as a fixed-point camera with respect to the vicinity and surroundings of the treatment site without moving. Because the second endoscope 30 is more distant from the imaging target site than the first endoscope 10, an amount by which the second endoscope 30 is moved in accordance with movement of the imaging part 12 of the first endoscope 10 is large. Because of this, in a case in which the second endoscope 30 is always moved following fine movement of the imaging part 12 of the first endoscope 10, the insertion part 31 of the second endoscope 30 moves a body wall or the like of the patient by a trocar in many cases, and the burden on the patient may be increased. In the present modified example, although field-of-view centers of the wide-angle image and the narrow-angle image are not always exactly matched, the deviation falls within an extent such that there is no problem in the treatment and observation. Because of this, in the present modified example, unnecessary operations of the second endoscope 30 can be reduced, and the burden on the patient can be reduced.

Further, in the present modified example, by reducing unnecessary operations of the second endoscope 30, operating noise during operation can be reduced.

Modified Example

A modified example of the present embodiment will be described.

In the endoscope system 3 of the present modified example, each of the first endoscope 10 and the second endoscope 30 has a distance measurer as in the second embodiment described above. The constitution of the distance measurer may be, for example, as in the second embodiment described above, that for capturing a set of two images having parallax with the left-side imaging part 61 and the right-side imaging part 62 and using the set of two images for measuring a distance. As in the second embodiment, the constitution of the distance measurer is not particularly limited also in the present modified example.

Further, taking into consideration a case in which a treatment site is hidden behind the imaging part 12 of the first endoscope 10 in a field of view of the imaging part 32 of the second endoscope 30, the control device 80 may calculate a distance between the imaging part 12 of the first endoscope 10 and the second endoscope 30 instead of a distance between the second endoscope 30 and the treatment site. In this case, a distance between the treatment site and the second endoscope 30 may be calculated on the basis of information of a distance between the first endoscope 10 and the treatment site and information of a distance between the imaging part 12 of the first endoscope 10 and the second endoscope 30.

In the endoscope system 3 of the present modified example, the control device 80 calculates a distance between the second endoscope 30 and an imaging target site thereof, and the control device 80 keeps the distance between the second endoscope 30 and the imaging target site thereof constant. Consequently, when the second endoscope 30 is moved by the second arm 71 following the movement of the imaging part 12 of the first endoscope 10, the distance between the second endoscope 30 and the imaging target site thereof does not change before and after movement of the second endoscope 30.

Fourth Embodiment

Figure 12:
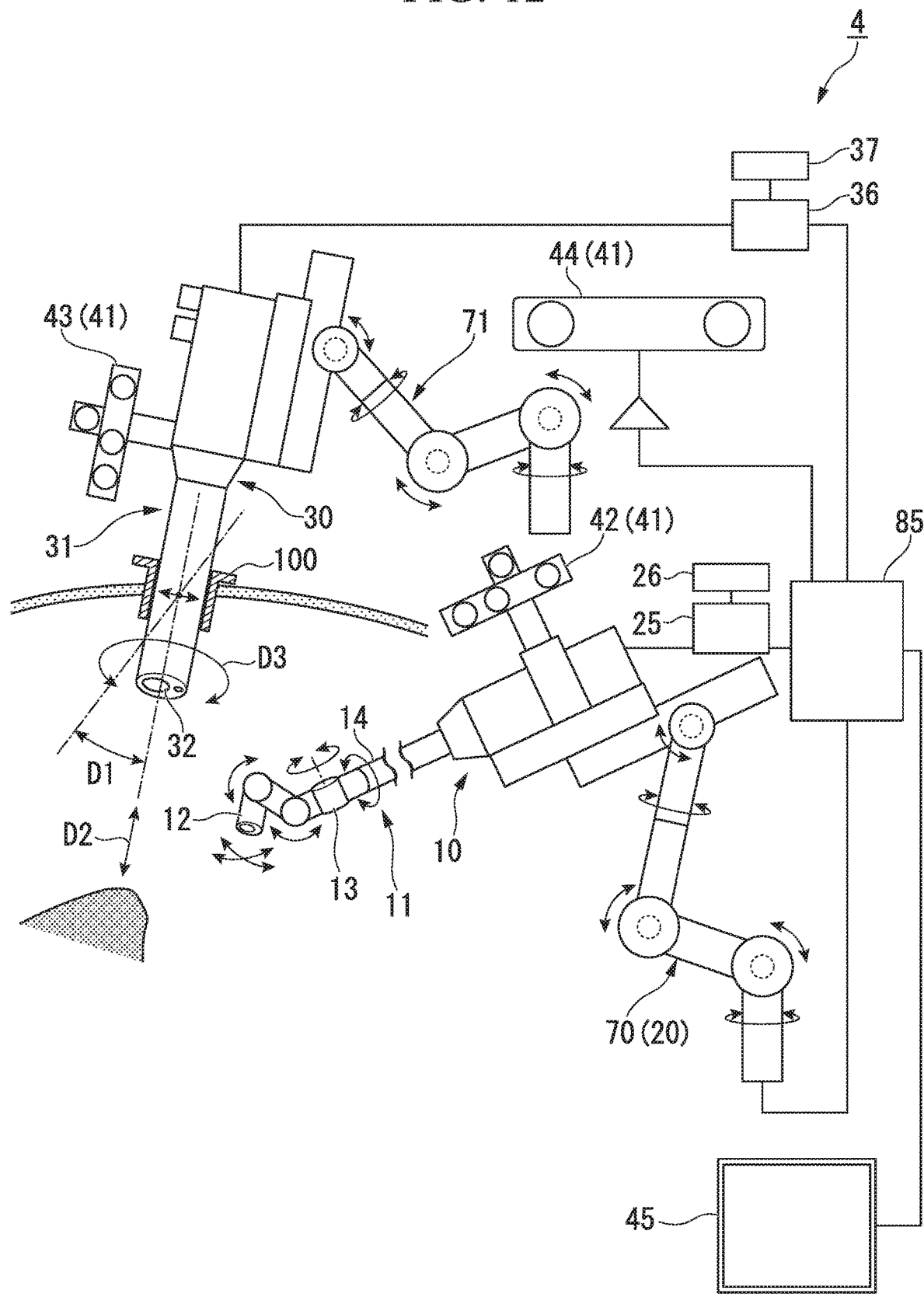
FIG. 12 is a schematic overall view illustrating an endoscope system according to a fourth embodiment of the present invention.
Figure 13:
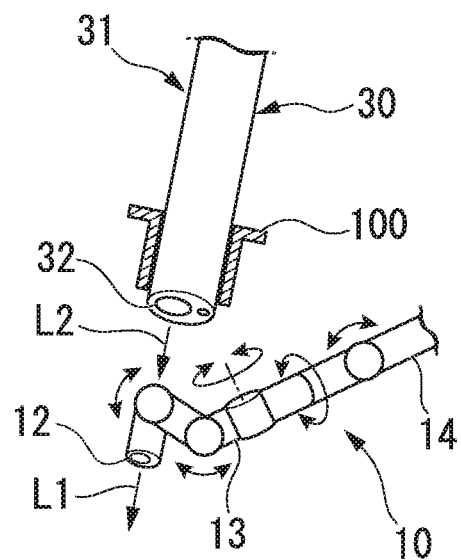
FIG. 13 is a schematic view describing an action of the endoscope system.
Figure 14:
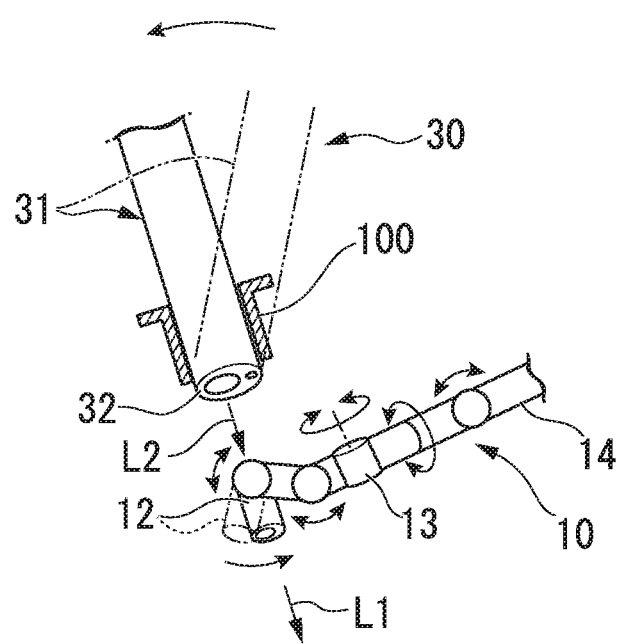
FIG. 14 is a schematic view describing an action of the endoscope system.
Figure 15:
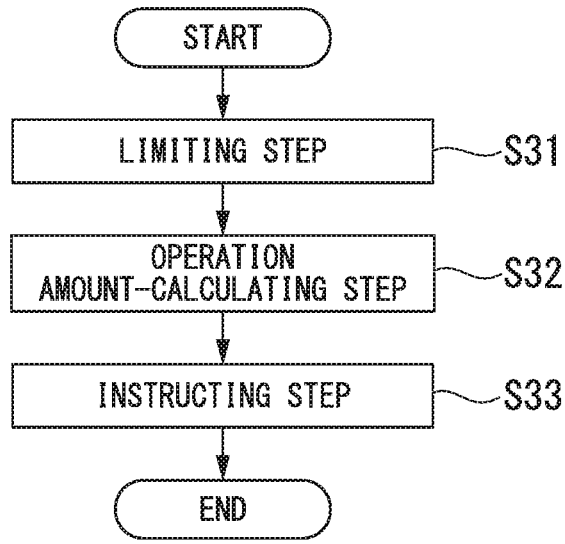
FIG. 15 is a flowchart illustrating a control procedure by a control device of the endoscope system.

A fourth embodiment of the present invention will be described. In the present embodiment, like reference numerals as in the above embodiments will be given to elements the same as those in the above embodiments, and overlapping descriptions will be omitted. FIG. 12 is a schematic overall view illustrating an endoscope system according to the present embodiment. FIGS. 13 and 14 are schematic views describing actions of the endoscope system. FIG. 15 is a flowchart illustrating a control procedure by a control device of the endoscope system.

An endoscope system 4 according to the present embodiment illustrated in FIG. 12 has, instead of the control device 80 disclosed in the third embodiment, a control device 85 capable of performing control in consideration of a case in which the second endoscope 30 cannot be moved to make the optical axis L2 of the imaging part 32 of the second endoscope 30 coaxial to the optical axis L1 of the imaging part 12 of the first endoscope 10. The constitution of the endoscope system 4 according to the present embodiment may be the same as that of the third embodiment except that the endoscope system 4 includes the different control device 85 instead of the control device 80 disclosed in the third embodiment. The control device 85 can be realized by hardware such as one or more Central Processing Unit (CPU), and by reading instructions stored on a computer readable storage device (also referenced throughout this disclosure as controller).

For example, in the third embodiment and the present embodiment, the imaging part 12 of the first endoscope 10 is movable by the first arm 70 and the joint part 13 whereas a movable scope of the imaging part 32 of the second endoscope 30 is limited by a movable range of the second arm 71. Further, in the third embodiment and the present embodiment, in a case in which the second endoscope 30 is inserted into the body via a trocar 100, although the insertion part 31 of the second endoscope 30 can easily perform an oscillating operation about the trocar 100 and an advancing-withdrawing operation with respect to the trocar, there is a limitation in an operation thereof requiring movement of the trocar 100 (see FIGS. 12 to 14).

In the present embodiment, the control device 85 limits the movable range of the second arm 71 for moving the second endoscope 30 to a range in which the insertion part 31 of the second endoscope 30 performs the oscillating operation about the trocar 100 (indicated with a mark D1 in FIG. 12), a range in which the insertion part 31 of the second endoscope 30 performs the advancing-withdrawing operation in the trocar 100 (indicated with a mark D2 in FIG. 12), and a range in which the insertion part 31 of the second endoscope 30 is rotated with a central axis of the trocar 100 as a center of rotation (indicated with a mark D3 in FIG. 12) (a limiting step, Step S31, see FIG. 15). In Step S31, the control device 85 calculates the position and direction of the optical axis L2 of the second endoscope 30 on the basis of the position and orientation of the second endoscope 30 located within the ranges of limitations described above. Further, the control device 85 may limit the movable range of the insertion part 31 of the second endoscope 30 in advance according to an arrangement of organs or other medical instruments in the body to prevent the insertion part 31 of the second endoscope 30 from colliding therewith.

Further, the control device 85 calculates an operation amount for moving the optical axis L2 of the second endoscope 30 in a direction in which the optical axis L2 is coaxial with the optical axis L1 of the first endoscope 10 (an operation amount-calculating step, Step S32, see FIG. 15). In Step S32, the control device 85 sets a movement target position and a movement target direction of the optical axis L2 of the second endoscope 30 so that an angle formed between a vector of the optical axis L1 of the imaging part 12 of the first endoscope 10 and a vector of the optical axis L2 of the imaging part 32 of the second endoscope 30 is minimized. Further, the control device 85 sets a movement path (operation amount) for operating the second arm 71 within the scope of the movable range limited by the limiting step.

After Step S32, the control device 85 outputs an operation instruction to the second arm 71 on the basis of the operation amount calculated in Step S32 (an instructing step, Step S33, see FIG. 15). According to the operation instruction output from the control device 85, the second arm 71 moves the optical axis L2 of the second endoscope 30 in the direction in which the optical axis L2 is coaxial with the optical axis L1 of the first endoscope 10.

According to the constitution of the present embodiment, the optical axis L1 of the second endoscope 30 is substantially parallel to the optical axis L1 of the first endoscope 10 even in a case in which the optical axis L2 is not coaxial with the optical axis L1 of the first endoscope 10. Because of this, in the present embodiment, a field-of-view center of an image captured by the imaging part 12 of the first endoscope 10 may be located substantially at the center of an imaging field of view of the imaging part 32 of the second endoscope 30.

Further, in the present embodiment, the control device 85 may operate the second arm 71 within the scope of movable range limited by the limiting step so that a distance between the optical axis L1 of the imaging part 12 of the first endoscope 10 and the optical axis L2 of the imaging part 32 of the second endoscope 30 is minimized. In this case, the optical axis L1 of the imaging part 12 of the first endoscope 10 and the optical axis L2 of the imaging part 32 of the second endoscope 30 may be brought close to each other to an extent such that the optical axis L1 and the optical axis L2 can be regarded as substantially coaxial.

Fifth Embodiment

Figure 16:
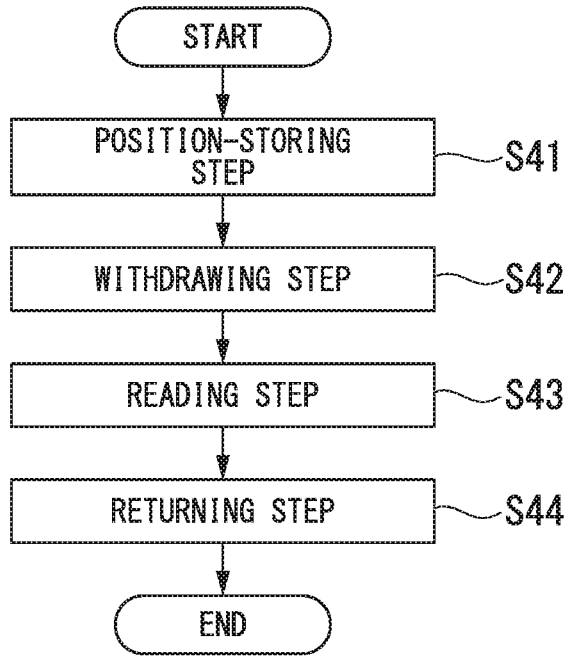
FIG. 16 is a flowchart illustrating a control procedure by a control device of an endoscope system according to a fifth embodiment of the present invention.
Figure 17:
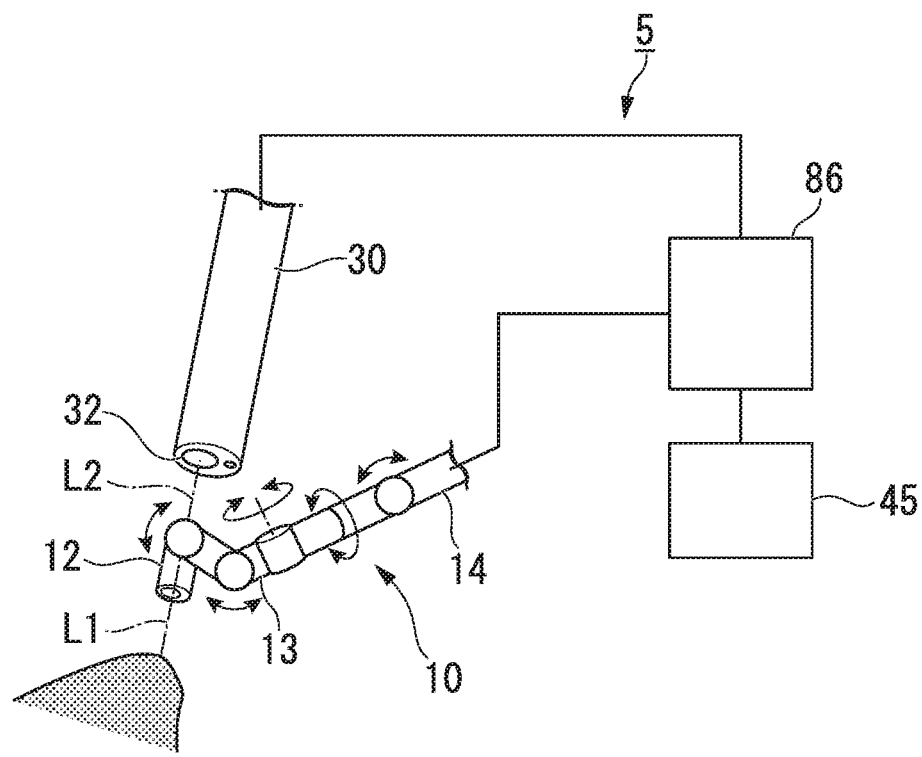
FIG. 17 is a schematic view describing an operation when the endoscope system is used.
Figure 18:
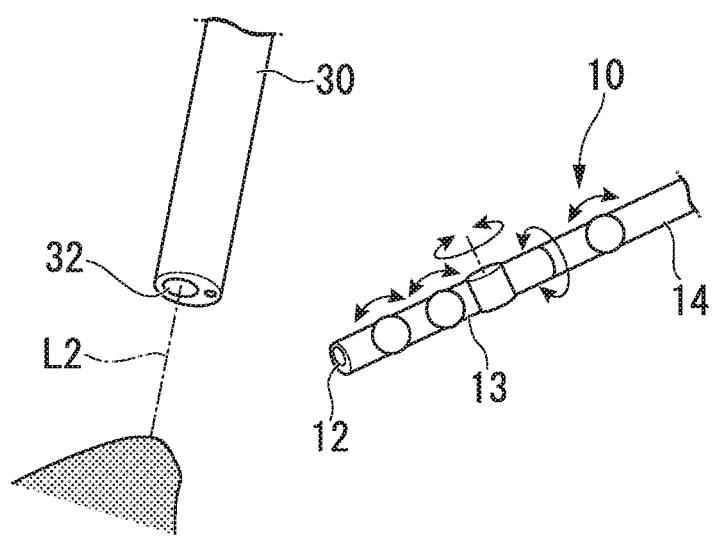
FIG. 18 is a schematic view describing an operation when the endoscope system is used.

A fifth embodiment of the present invention will be described. In the present embodiment, like reference numerals as in the above embodiments will be given to elements the same as those in the above embodiments, and overlapping descriptions will be omitted. FIG. 16 is a flowchart illustrating a control procedure by a control device 86 of an endoscope system according to the present embodiment. FIGS. 17 and 18 are schematic views describing operations when an endoscope system is used.

An endoscope system 5 according to the present embodiment (see FIG. 17) includes the first endoscope 10, the arm 20, and the second endoscope 30 (see FIG. 1) which are the same as those in the first embodiment and the control device 86 (see FIG. 17) for controlling operations of the first endoscope 10 and the arm 20.

The control device 86 has a control procedure different from the control procedure included in the control device 50 of the first embodiment described above. Hereinafter, the constitution of the control device 86 will be described by showing a control procedure of a main part in the endoscope system 5 according to the present embodiment.

When an input is made to the viewpoint change switch 39 (see FIG. 1) so that an image displayed on the main monitor 45 is an image from the second endoscope 30, the control device 86 of the present embodiment moves the imaging part 12 of the first endoscope 10 by the following steps from Step S41 to Step S44.

First, the control device 86 stores a current position and orientation of the first endoscope 10 (see FIG. 17) on the basis of the input made to the viewpoint change switch 39 (a position-storing step, Step S41, see FIG. 16).

After Step S41, the control device 86 moves the insertion part 11 of the first endoscope 10 by a predetermined distance in a direction in which the insertion part 11 of the first endoscope 10 is withdrawn outside of the body (a withdrawing step, Step S42, see FIG. 16).

In Step S42, the control device 86 drives the joint part 13 to be linear in order from a proximal end side of the joint part 13 (see FIG. 18) by interlocking with the movement of the insertion part 11 of the first endoscope 10 being withdrawn outside of the body so that the joint part 13 or the imaging part 12 does not come into contact with a tissue in the vicinity of a treatment site. Further, in Step S42, the control device 86 may move the insertion part 11 of the first endoscope 10 in the direction in which the insertion part 11 of the first endoscope 10 is withdrawn outside of the body while the shape of the joint part 13 is maintained.

The movement of the insertion part 11 of the first endoscope 10 in Step S42 is performed by the control device 86 controlling an operation of each of the joint parts 22 of the arm 20.

Through Step S42, the imaging part 12 of the first endoscope 10 moves to a position away from the optical axis L2 of the imaging part 32 of the second endoscope 30. A movement destination of the imaging part 12 of the first endoscope 10 in Step S42 is, for example, outside an imaging field of view of the imaging part 32 of the second endoscope 30 or a position within the imaging field of view of the imaging part 32 of the second endoscope 30 at which observation using the second endoscope 30 is not interfered with.

This completes Step S42.

In a state in which Step S42 is completed, because the imaging part 12 of the first endoscope 10 is not located at a central portion of the imaging field of view of the imaging part 32 of the second endoscope 30, states of the treatment site and the vicinity thereof can be suitably observed by the imaging part 32 of the second endoscope 30.

In the present embodiment, in a case in which observation using the imaging part 32 of the second endoscope 30 is completed and then treatment on the treatment site is resumed, the imaging part 12 of the first endoscope 10 that is moved in Step S42 described above is moved to the position stored in Step S41.

For example, in a case in which treatment on the treatment site is resumed, the operator makes an input to the viewpoint change switch 39 as an input for switching the image displayed on the main monitor 45 to an image captured by the imaging part 12 of the first endoscope 10.

On the basis of the input made to the viewpoint change switch 39, the control device 86 reads out the position and orientation of the first endoscope 10 stored in Step S41 above (a reading step, Step S43, see FIG. 16).

After Step S43, the control device 86 outputs an operation instruction to the first endoscope 10 and the arm 20 so that the position and orientation of the first endoscope 10 become the position and orientation read out in Step S43 above (a returning step, Step S44, see FIG. 16).

Through Step S43 and Step S44 above, the imaging part 12 of the first endoscope 10 may be returned to the position stored before movement in Step S41 (see FIG. 17) and capture a narrow-angle image capturing the treatment site at a field-of-view center in the orientation before movement.

As described above, according to the endoscope system 5 according to the present embodiment, by causing the imaging part 12 of the first endoscope 10 to withdraw from a field-of-view center of a wide-angle image captured using the second endoscope 30, the treatment site in the vicinity of the field-of-view center of the wide-angle image and surroundings thereof may be suitably observed. Further, after the observation using the wide-angle image, because the imaging part 12 of the first endoscope 10 can be automatically returned to its original state from the withdrawn state, the operational burden on the operator can be reduced.

Sixth Embodiment

Figure 19:
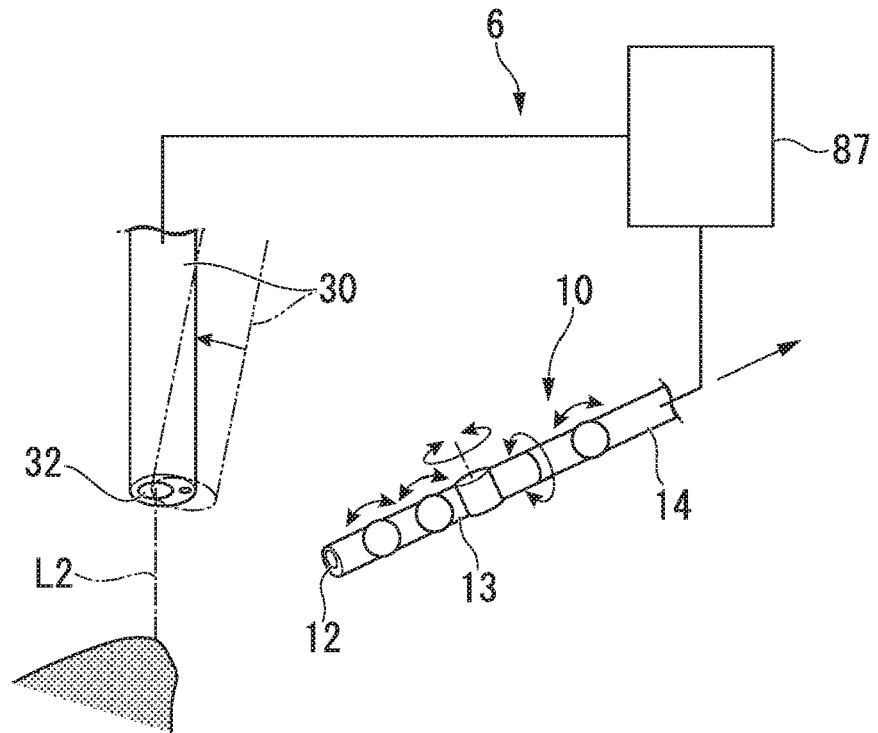
FIG. 19 is a schematic view describing an operation when an endoscope system according to a sixth embodiment of the present invention is used.
Figure 20:
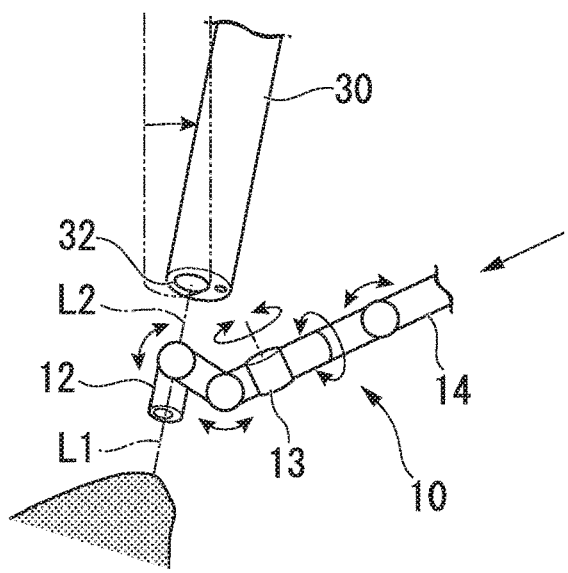
FIG. 20 is a schematic view describing an operation when the endoscope system is used.

A sixth embodiment of the present invention will be described. In the present embodiment, like reference numerals as in the above embodiments will be given to elements the same as those in the above embodiments, and overlapping descriptions will be omitted. FIG. 19 is a schematic view describing an operation when an endoscope system according to the present embodiment is used. FIG. 20 is a schematic view describing an operation when the endoscope system is used.

An endoscope system 6 according to the present embodiment (see FIG. 19) includes the first endoscope 10, the second endoscope 30, the first arm 70, and the second arm 71 (see FIG. 10) which are the same as those in the third embodiment and a control device 87 (see FIG. 19) for controlling operations of the first endoscope 10, the first arm 70, and the second arm 71.

The control device 87 is different from the constitution of the fifth embodiment in that the control device 87 has a control procedure different from that of the control device 86 of the first embodiment described above.

As in the steps from Step S41 to Step S44 disclosed in the fifth embodiment, the control device 87 first causes the imaging part 12 of the first endoscope 10 to withdraw when the operator switches a narrow-angle image of the first endoscope 10 to a wide-angle image of the second endoscope 30 (see FIG. 19) and then returns the imaging part 12 of the first endoscope 10 to its original position when the operator switches a wide-angle image of the second endoscope 30 to a narrow-angle image of the first endoscope 10.

Further, after returning the imaging part 12 of the first endoscope 10 to its original position and displaying the narrow-angle image on the main monitor 45, as in the steps from Step S21 to Step S24 disclosed in the third embodiment above, the control device 87 of the present embodiment moves the second arm 71 so that the optical axis L1 of the imaging part 12 of the first endoscope 10 and the optical axis L2 of the imaging part 32 of the second endoscope 30 are coaxial (see FIG. 20).

According to the endoscope system 6 according to the present embodiment, because the imaging part 12 of the first endoscope 10 may be caused to withdraw from a treatment site in a case in which the treatment site and the surroundings thereof are observed from a panoramic view using the wide-angle image of the imaging target site using the second endoscope 30, the imaging part 12 of the first endoscope 10 does not interfere in a case in which the treatment site is observed using the second endoscope 30.

Further, in the endoscope system 6 according to the present embodiment, when the operator observes the surroundings of the treatment site by moving the second endoscope 30 and then returns the image displayed on the main monitor 45 to the narrow-angle image, the imaging part 12 of the first endoscope 10 moves from the withdrawn position to a position at which the treatment site is captured at a field-of-view center and returns to its original state. The imaging part 32 of the second endoscope 30 of the endoscope system 6 is moved by the second arm 71 in the background to be coaxial with the optical axis L1 of the imaging part 12 of the first endoscope 10. As a result, the control device 87 may automatically move the first endoscope 10 and the second endoscope 30 so that both the imaging part 12 of the first endoscope 10 and the imaging part 32 of the second endoscope 30 capture the treatment site at the field-of-view centers. Consequently, according to the endoscope system 6 according to the present embodiment, the operational burden on the operator can be reduced.

Seventh Embodiment

Figure 21:
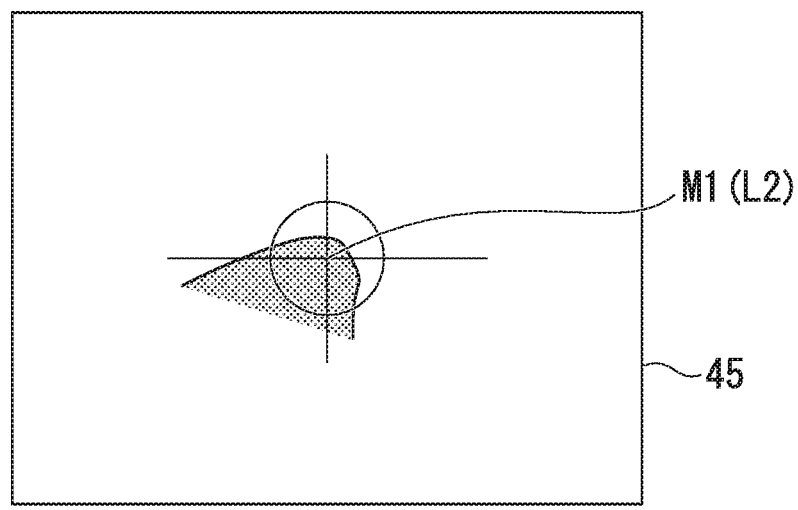
FIG. 21 is a schematic view illustrating an example of an image displayed on a main monitor of an endoscope system according to a seventh embodiment of the present invention.
Figure 22:
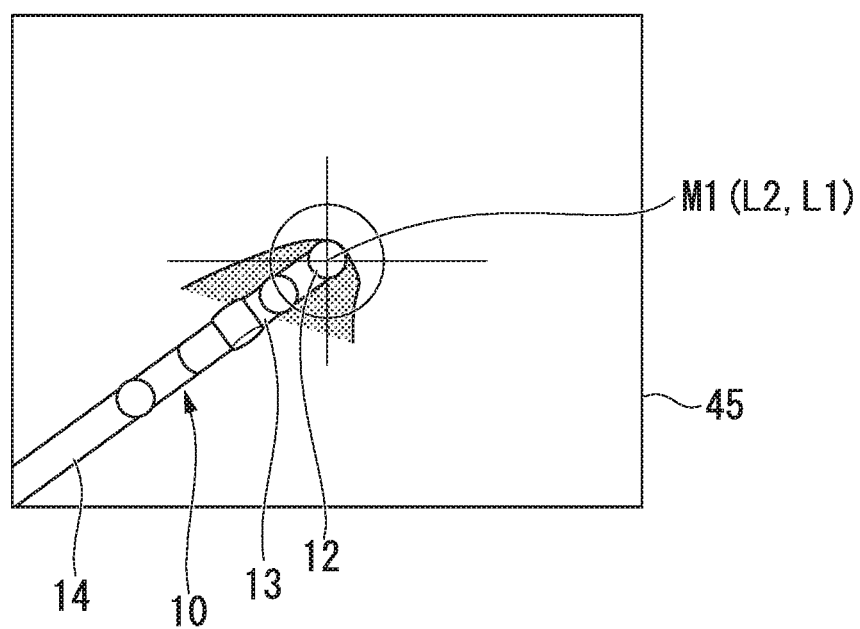
FIG. 22 is a schematic view illustrating an example of an image displayed on the main monitor of the endoscope system.

A seventh embodiment of the present invention will be described. In the present embodiment, like reference numerals as in the above embodiments will be given to elements the same as those in the above embodiments, and overlapping descriptions will be omitted. FIGS. 21 and 22 are schematic views illustrating examples of an image displayed on a main monitor of an endoscope system according to the present embodiment.

An endoscope system 7 according to the present embodiment includes a control device 89 having a constitution different from that of the control device 50 disclosed in the first embodiment instead of the control device 50 of the first embodiment (see FIG. 1). The constitution of the endoscope system 7 according to the present embodiment is the same as that of the first embodiment described above except for the constitution of the control device 89 (also referenced throughout this disclosure as controller). The control device 89 can be realized by hardware such as one or more Central Processing Unit (CPU), and by reading instructions stored on a computer readable storage device. The control device 89 of the endoscope system 7 according to the present embodiment may display a position of the optical axis L2 of the second endoscope 30 on the main monitor 45. As a specific example, as illustrated in FIG. 21, the control device 89 of the present embodiment outputs an image captured by the imaging part 32 of the second endoscope 30 on the main monitor 45 by superimposing an image of a predetermined target mark M1 at the field-of-view center of the image.

When the endoscope system 7 according to the present embodiment is used, in a case in which the operator adjusts positions of the first endoscope 10 and the second endoscope 30 so that both the imaging part 12 of the first endoscope 10 and the imaging part 32 of the second endoscope 30 capture the treatment site at the field-of-view centers, the operator first observes the image captured by the imaging part 32 of the second endoscope 30 as in the first embodiment.

Here, in the present embodiment, because the image captured by the imaging part 32 of the second endoscope 30 and the target mark M1 are displayed on the main monitor 45 as illustrated in FIG. 21, the operator can easily grasp where the optical axis L2 of the imaging part 32 of the second endoscope 30 is located in the imaging target site.

Because of this, by moving the second endoscope 30 so that the target mark M1 is superimposed on the treatment site as illustrated in FIG. 22, the operator can accurately designate where to move the imaging part 12 of the first endoscope 10.

When the first endoscope 10 is operated by the control device 89 as in the first embodiment in a state in which a target mark M2 is superimposed on the treatment site, the imaging part 12 of the first endoscope 10 moves to a position superimposed on the target mark. Because the position of the target mark M2 is a position reflecting a position determined by the operator as a treatment target, the imaging part 12 of the first endoscope 10 acquires an image capturing the position determined by the operator at a field-of-view center.

When the imaging part 12 of the first endoscope 10 is moved to the position superimposed on the target mark, an image captured by the imaging part 12 of the first endoscope 10 is displayed on the main monitor 45. Consequently, the operator can perform a treatment on the treatment site using the image captured by the imaging part 12 of the first endoscope 10.

In this way, because the control device 89 superimposes the target mark on the image captured by the imaging part 32 of the second endoscope 30 and displays the superimposed target mark and the image on the main monitor 45, it is easy to move the second endoscope 30 so that the optical axis L2 of the imaging part 32 of the second endoscope 30 is made to coincide with the treatment site. As a result, the operator can easily create a state in which both the imaging part 32 of the second endoscope 30 and the imaging part 12 of the first endoscope 10 capture the treatment site at the field-of-view centers with high accuracy.

Modified Example

Figure 23:
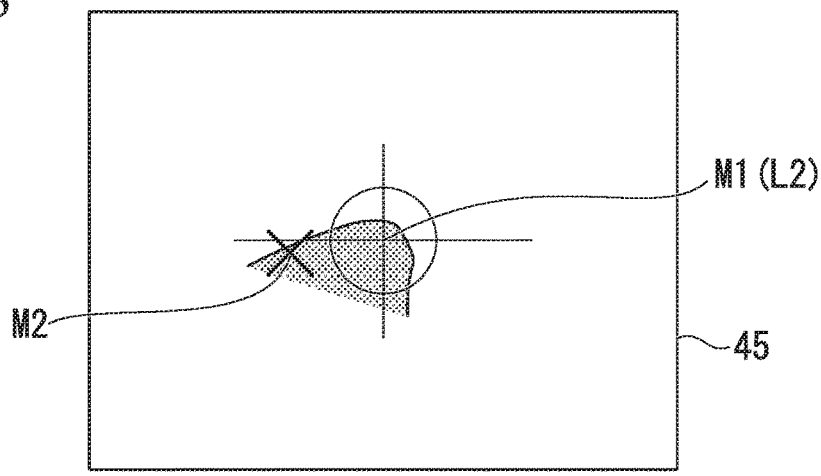
FIG. 23 is a schematic view illustrating an example of an image displayed on the main monitor of the endoscope system.
Figure 24:
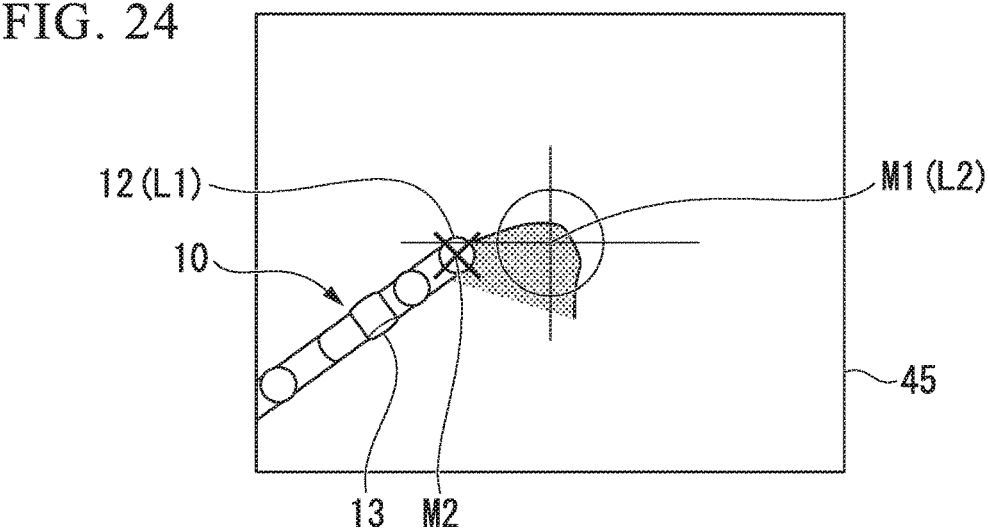
FIG. 24 is a schematic view illustrating an example of an image displayed on the main monitor of the endoscope system.
Figure 25:
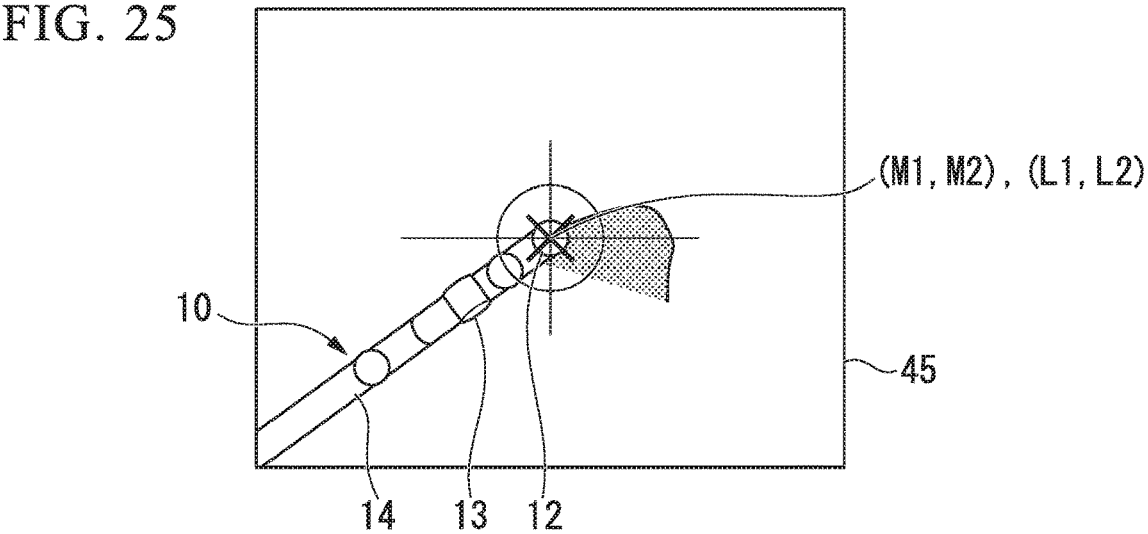
FIG. 25 is a schematic view illustrating an example of an image displayed on the main monitor of the endoscope system.

A modified example of the present embodiment will be described. FIGS. 23 to 25 are schematic views illustrating examples of an image displayed on the main monitor of the endoscope system of the present modified example.

In the present modified example, the target mark is an arbitrary point designated by the operator on the image captured by the imaging part 32 of the second endoscope 30 instead of the optical axis L2 of the second endoscope 30.

As illustrated in FIG. 23, in the present modified example, both a first mark M1 indicating a field-of-view center of the second endoscope 30 and a second mark M2, which is a target mark in the present modified example, are displayed on the main monitor 45.

As a specific example, the control device 89 moves the first endoscope 10 so that the optical axis L2 of the imaging part 32 of the second endoscope 30 and the optical axis L1 of the first endoscope 10 are parallel to each other, and moves the imaging part 12 of the first endoscope 10 so that the optical axis L1 of the first endoscope 10 is superimposed on a target mark (the second mark M2) on the image by the imaging part 32 of the second endoscope 30 (see FIG. 24).

Then, by the control device 89 displaying the image captured by the imaging part 12 of the first endoscope 10 on the main monitor 45, a narrow-angle image including a position corresponding to the target mark (the second mark M2) at a field-of-view center is displayed on the main monitor 45.

In the present modified example, in a case in which a treatment site is set at a site other than the field-of-view center in the image captured by the imaging part 32 of the second endoscope 30, by designating the position of the target mark (the second mark M2) without moving the second endoscope 30, the first endoscope 10 can be operated so that the imaging part 12 of the first endoscope 10 can capture an image capturing the treatment site at the field-of-view center.

By combining the constitution of the present modified example with the constitution of the third embodiment, the second endoscope 30 may be moved so that the optical axis L2 of the imaging part 32 of the second endoscope 30 is coaxial with the optical axis L1 of the imaging part 12 of the first endoscope 10 in the state in which the imaging part 12 of the first endoscope 10 captures the treatment site at the field-of-view center (see FIG. 25).

Although embodiments of the present invention have been described in detail above with reference to the drawings, specific constitutions of the present invention are not limited to the embodiments, and design changes and the like within the scope that does not depart from the gist of the present invention are also included.

Further, a first marker may include information that serves as a basis for specifying a position of an optical axis of an imaging part of a first endoscope. The information may be, for example, a unique identifier encoded to a model of the first endoscope. In this case, a control device may recognize the position of the optical axis based on a structure of the first endoscope on the basis of the identifier included in the first marker.

Likewise, a second marker may include information that serves as a basis for specifying a position of an optical axis of an imaging part of a second endoscope. In this case, the control device may recognize the position of the optical axis based on a structure of the second endoscope on the basis of the identifier included in the second marker.

The elements shown in each of the embodiments and modified examples described above may be suitably combined. Further, design changes and the like to the specific constitutions are not limited to the above.

What is claimed is:
1. A medical system comprising:
   a first insertable instrument comprising a first image sensor;
   a second insertable instrument comprising a second image sensor;
   an arm configured to support and move the first insertable instrument; and
   a controller configured to:
      acquire a position and orientation of the second insertable instrument in a predetermined coordinate system;
      calculate a position and direction of an optical axis of the second image sensor based on the position and orientation of the second insertable instrument;
      acquire a position and orientation of the first insertable instrument in the predetermined coordinate system;
      calculate a first operation amount of the arm to move the first image sensor such that the optical axis of the second image sensor substantially coincides with an optical axis of the first image sensor to make a field-of-view center of the first image sensor and a field-of-view center of the second image sensor coincide with each other, based on the position and orientation of the first insertable instrument;
      control the arm, based on the first operation amount of the arm, to move the first insertable instrument; and
      after controlling the arm, based on the first operation amount of the arm, to move the first insertable instrument, control the arm to move the first insert- able instrument such that the first insertable instrument is withdrawn from the field-of-view center of the second image sensor.

2. The medical system according to claim 1,
wherein the controller is configured to store a position and orientation of the first insertable instrument where the optical axis of the second image sensor coincides with the optical axis of the first image sensor.

3. The medical system according to claim 2,
wherein the controller is configured to, after controlling the arm to move the first insertable instrument such that the first insertable instrument is withdrawn from the field-of-view center of the second image sensor, control the arm to move the first insertable instrument to the stored position and orientation such that the optical axis of the second image sensor substantially coincides with the optical axis of the first image sensor.

4. A controller for controlling a medical system comprising:
a first insertable instrument comprising a first image sensor;
a second insertable instrument comprising a second image sensor; and
an arm configured to support and move the first insertable instrument,
wherein the controller comprises one or more processors configured to:
acquire a position and orientation of the second insertable instrument in a predetermined coordinate system;
calculate a position and direction of an optical axis of the second image sensor based on the position and orientation of the second insertable instrument;
acquire a position and orientation of the first insertable instrument in the predetermined coordinate system;
calculate a first operation amount of the arm to move the first image sensor such that the optical axis of the second image sensor substantially coincides with an optical axis of the first image sensor to make a field-of-view center of the first image sensor and a field-of-view center of the second image sensor coincide with each other, based on the position and orientation of the first insertable instrument;
control the arm, based on the first operation amount of the arm, to move the first insertable instrument; and
after controlling the arm, based on the first operation amount of the arm, to move the first insertable instrument, control the arm to move the first insertable instrument such that the first insertable instrument is withdrawn from the field-of-view center of the second image sensor.

5. The controller according to claim 4,
wherein the one or more processors are configured to store a position and orientation of the first insertable instrument where the optical axis of the second image sensor coincides with the optical axis of the first image sensor.

6. The controller according to claim 5,
wherein the one or more processors are configured to, after controlling the arm to move the first insertable instrument such that the first insertable instrument is withdrawn from the field-of-view center of the second image sensor, control the arm to move the first insertable instrument to the stored position and orientation such that the optical axis of the second image sensor substantially coincides with the optical axis of the first image sensor.

7. A computer readable storage device storing instructions for controlling a medical system comprising:
a first insertable instrument comprising a first image sensor;
a second insertable instrument comprising a second image sensor; and
an arm configured to support and move the first insertable instrument,
wherein the instructions cause a computer to perform processes comprising:
acquiring a position and orientation of the second insertable instrument in a predetermined coordinate system;
calculating a position and direction of an optical axis of the second image sensor based on the position and orientation of the second insertable instrument;
acquiring a position and orientation of the first insertable instrument in the predetermined coordinate system;
calculating a first operation amount of the arm to move the first image sensor such that the optical axis of the second image sensor substantially coincides with an optical axis of the first image sensor to make a field-of-view center of the first image sensor and a field-of-view center of the second image sensor coincide with each other, based on the position and orientation of the first insertable instrument;
controlling the arm, based on the first operation amount of the arm, to move the first insertable instrument; and
after controlling the arm, based on the first operation amount of the arm, to move the first insertable instrument, controlling the arm to move the first insertable instrument such that the first insertable instrument is withdrawn from the field-of-view center of the second image sensor.

8. The computer readable storage device according to claim 7,
wherein the instructions cause the computer to further perform processes comprising storing a position and orientation of the first insertable instrument where the optical axis of the second image sensor coincides with the optical axis of the first image sensor.

9. The computer readable storage device according to claim 8,
wherein the instructions cause the computer to further perform processes comprising, after controlling the arm to move the first insertable instrument such that the first insertable instrument is withdrawn from the field-of-view center of the second image sensor, controlling the arm to move the first insertable instrument to the stored position and orientation such that the optical axis of the second image sensor substantially coincides with the optical axis of the first image sensor.

* * * * *